United States Patent
Kasugai

(10) Patent No.: US 12,239,199 B2
(45) Date of Patent: Mar. 4, 2025

(54) HAIR CUTTING MEMBER AND HAIR CUTTING DEVICE

(71) Applicant: Panasonic Intellectual Property Management Co., Ltd., Osaka (JP)

(72) Inventor: Hideki Kasugai, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 419 days.

(21) Appl. No.: 17/776,525

(22) PCT Filed: Nov. 5, 2020

(86) PCT No.: PCT/JP2020/041369
§ 371 (c)(1),
(2) Date: May 12, 2022

(87) PCT Pub. No.: WO2021/131342
PCT Pub. Date: Jul. 1, 2021

(65) Prior Publication Data
US 2022/0378168 A1 Dec. 1, 2022

(30) Foreign Application Priority Data
Dec. 25, 2019 (JP) .................. 2019-234944

(51) Int. Cl.
*A45D 26/00* (2006.01)
*G02B 6/42* (2006.01)
(52) U.S. Cl.
CPC ............. *A45D 26/00* (2013.01); *G02B 6/42* (2013.01); *A45D 2026/008* (2013.01)
(58) Field of Classification Search
CPC .... A45D 26/00; A45D 2026/008; G02B 6/42; G02B 6/3624; A61B 18/203
See application file for complete search history.

(56) References Cited

U.S. PATENT DOCUMENTS 4,362,356 A * 12/1982 Williams ............. G02B 6/3861
385/80
2014/0276685 A1 9/2014 Gustavsson et al.
(Continued)

FOREIGN PATENT DOCUMENTS

JP 2016-514491 A 5/2016
WO 2014/143670 A1 9/2014

OTHER PUBLICATIONS

International Search Report dated Dec. 28, 2020 issued in International Patent Application No. PCT/JP2020/041369, with English translation.

*Primary Examiner* — Scott M. Getzow
(74) *Attorney, Agent, or Firm* — Rimon P.C.

(57) ABSTRACT

A hair cutting member includes an optical waveguide, a connecting member, and a bonding member. The optical waveguide includes a core and a cladding that covers at least a portion of the core. The optical waveguide is disposed so as to emit light to hair growing on a skin. The connecting member retains an end of the optical waveguide. The bonding member bonds the optical waveguide and the connecting member to each other. The core is disposed off-center toward the outer circumference of the cladding. When viewed from an end face of the connecting member, a first distance between a center of the end face and an optical axis of the core is shorter than a second distance between the center of the end face and a center of the cladding. The technology of the present disclosure makes it possible to adjust the optical system of a hair cutting device easily.

9 Claims, 14 Drawing Sheets

(56) References Cited

U.S. PATENT DOCUMENTS

2015/0223889 A1    8/2015    Gustavsson et al.
2017/0209214 A1    7/2017    Gustavsson et al.
2021/0282852 A1*  9/2021    Moeskops ............ A61B 18/203

* cited by examiner

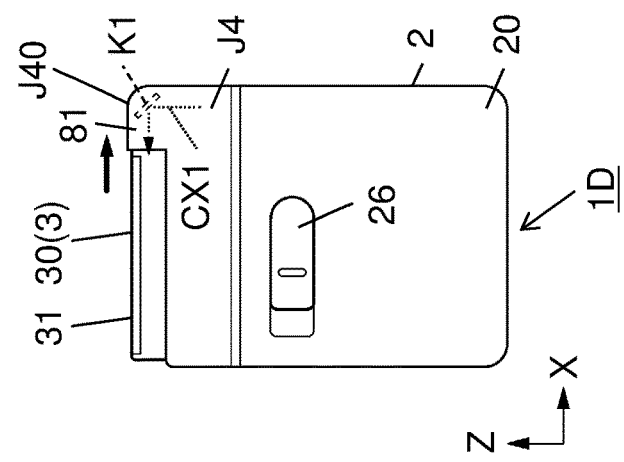
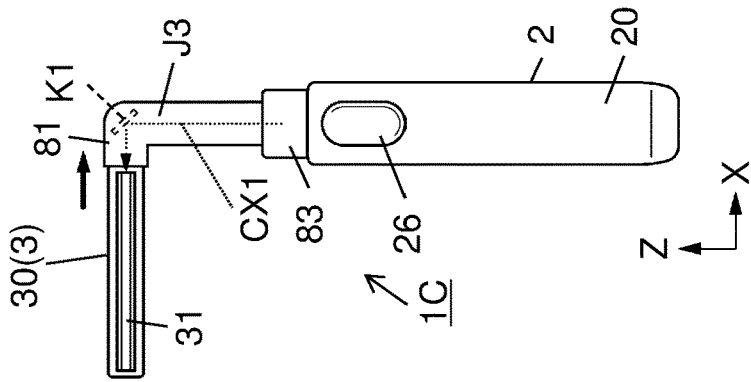
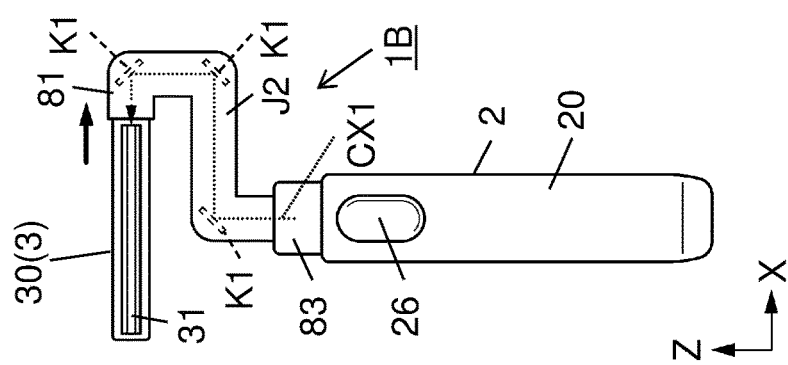
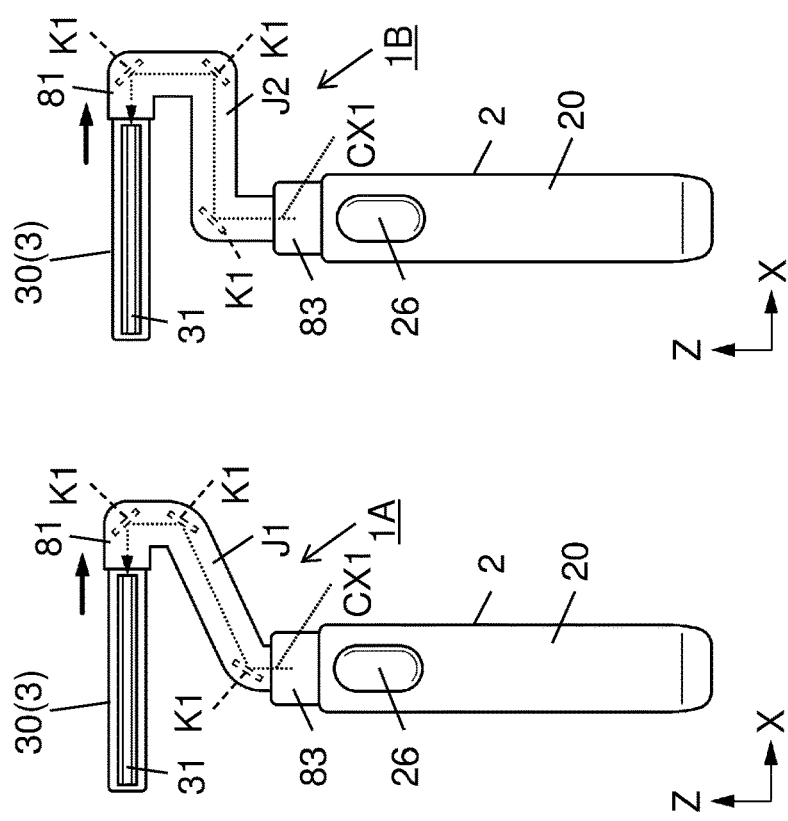

HAIR CUTTING MEMBER AND HAIR CUTTING DEVICE

CROSS-REFERENCE OF RELATED APPLICATIONS

This application is the U.S. National Phase under 35 U.S.C. § 371 of International Patent Application No. PCT/JP2020/041369, filed on Nov. 5, 2020, which in turn claims the benefit of Japanese Patent Application No. 2019-234944, filed on Dec. 25, 2019, the entire disclosures of which Applications are incorporated by reference herein.

BACKGROUND

Technical Field

The present disclosure relates to a hair cutting device that cuts hair by applying light to the hair.

Background Art

Patent Literature 1 (PTL 1) discloses an apparatus configured to cut hair using laser light. The apparatus disclosed in PTL 1 includes a laser light source and a fiber optic. The laser light source is configured to generate laser light having a wavelength selected to target a predetermined chromophore to effectively cut hair.

The fiber optic includes a proximal end, a distal end, an outer wall, and a cutting region positioned towards the distal end and extending along a portion of the side wall. The fiber optic receives the laser light from the laser light source at the proximal end and conducts the laser light from the proximal end toward the distal end. The fiber optic emits the light out of the cutting region and toward hair when the cutting region is brought in contact with the hair.

CITATION LIST

Patent Literature

PTL 1: Japanese Translation of PCT Publication No. 2016-514491

SUMMARY

The configuration disclosed in PTL 1 needs improvement in terms of adjustment of the optical system, in seeking practical application of a hair cutting device that utilizes light.

The present disclosure has been accomplished in view of the above circumstances, and it is an object of the present disclosure to adjust the optical system easily in a hair cutting member and a hair cutting device that make adjustment of the optical system easier.

In one embodiment of the present disclosure, a hair cutting member includes an optical waveguide, a connecting member, and a bonding member. The optical waveguide includes a core and a cladding covering at least a portion of the core. The optical waveguide is disposed so as to emit light to hair growing on a skin.

The connecting member retains an end of the optical waveguide. The bonding member bonds the optical waveguide and the connecting member to each other. The core is disposed off-center toward an outer circumference of the cladding. When viewed from an end face of the connecting member, a first distance between a center of the end face and an optical axis of the core is shorter than a second distance between the center of the end face and a center of the cladding.

According to another embodiment of the present disclosure, a hair cutting device includes the above-described hair cutting member and a device body. The device body includes a connection target, a light source, an optical system, and a case. To the connection target, a connecting member is mechanically connected. The light source generates light that is to be introduced into the core. The optical system is disposed between the light source and the connection target. The case is capable of accommodating the light source and the optical system.

The technology of the present disclosure makes it possible to adjust the optical system of a hair cutting device easily.

BRIEF DESCRIPTION OF DRAWINGS

FIG. 11A is a schematic view illustrating an external appearance of a hair cutting device according to a first modified example of the exemplary embodiment.

FIG. 11B is a schematic view illustrating an external appearance of a hair cutting device according to the first modified example of the exemplary embodiment.

FIG. 11C is a schematic view illustrating an external appearance of a hair cutting device according to the first modified example of the exemplary embodiment.

FIG. 11D is a schematic view illustrating an external appearance of a hair cutting device according to the first modified example of the exemplary embodiment.

DESCRIPTION OF EMBODIMENTS

1. Outline

An outline of hair cutting member 3 and hair cutting device 1 according to an exemplary embodiment of the present disclosure will be described below with reference to FIGS. 1 to 6B. Hair cutting device 1 is a device that cuts hair 91 (see FIG. 6A) by applying light to hair 91.

Figure 6A:
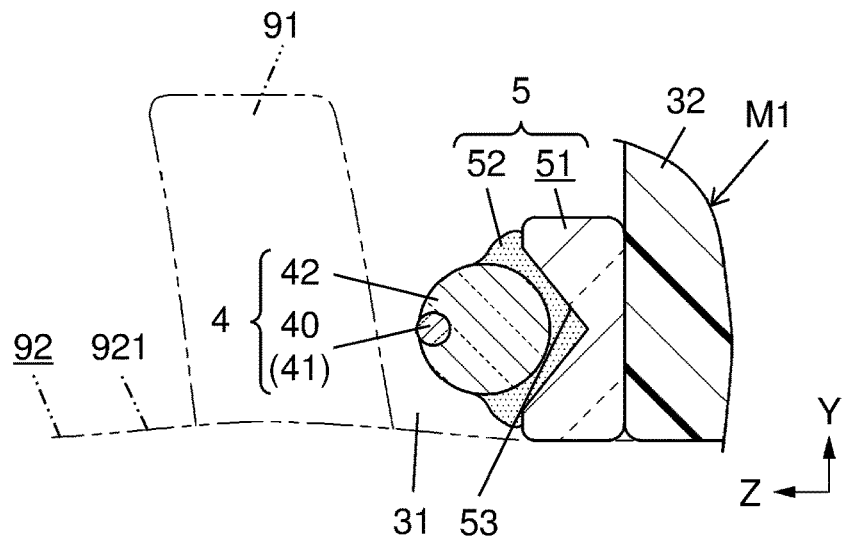
FIG. 6A is a schematic cross-sectional view illustrating the configuration of a major part of the hair cutting device according to the exemplary embodiment.

Hair 91, which is to be cut, is human facial hair, for example. Hair 91 is not limited thereto and may include various types of hair growing on human skin 92, such as arm hair and leg hair. In FIG. 6A, hair 91 and skin 92 are indicated by imaginary lines (dash-dot-dot lines).

Unlike common razors or scissors, hair cutting device 1 cuts hair 91 by applying optical energy to hair 91. Compared to common razors and scissors, hair cutting device 1 is less likely to damage skin 92 around hair 91. Hair cutting device 1 is less prone to physical deterioration, such as cutting edge damages.

Figure 1:
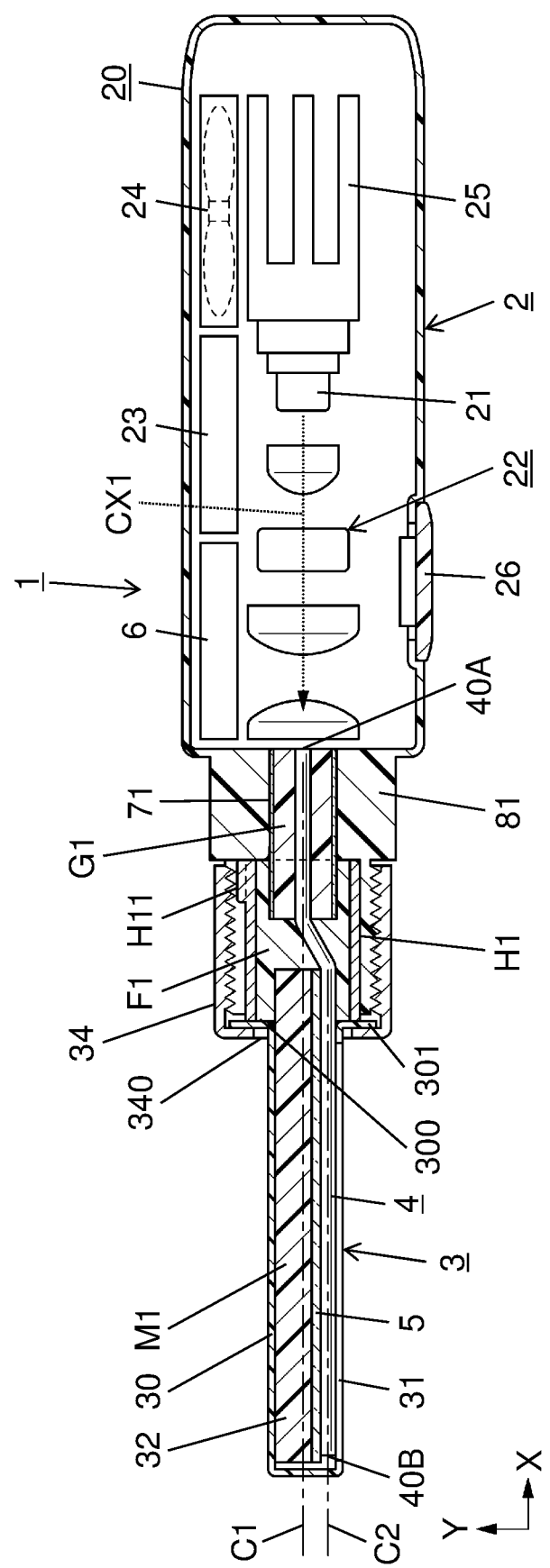
FIG. 1 is a cross-sectional view illustrating a hair cutting device according to an exemplary embodiment of the present disclosure, showing a state in which a hair cutting member is mounted to a device body.
Figure 2:
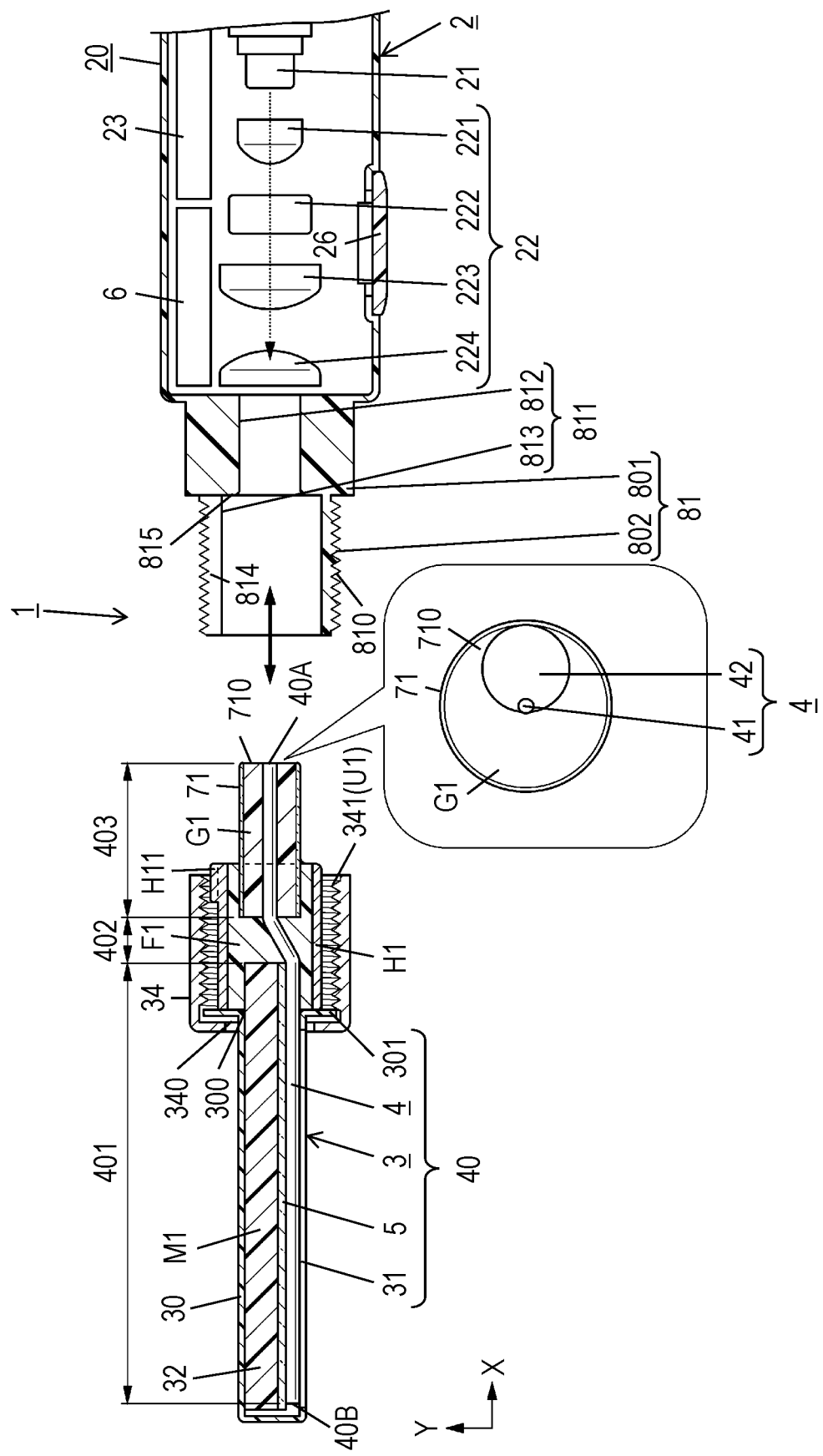
FIG. 2 is a cross-sectional view illustrating the hair cutting device according to the exemplary embodiment, showing a state in which the hair cutting member is detached from the device body.

FIGS. 1 and 2 are cross-sectional views of hair cutting device 1. FIG. 1 shows a state in which hair cutting member 3 is attached to device body 2. FIG. 2 shows a state in which hair cutting member 3 is detached from device body 2.

As illustrated in FIGS. 1 and 2, hair cutting device 1 includes hair cutting member 3 and device body 2. In the present exemplary embodiment, hair cutting member 3 corresponds to a head of hair cutting device 1, and device body 2 corresponds to a grip of hair cutting device 1.

As illustrated in FIGS. 1 and 2, hair cutting member 3 includes light emitting module M1 and a connecting member. In the present exemplary embodiment, the connecting member is ferrule 71. Light emitting module M1 includes optical waveguide 4 and retaining member 5. Optical waveguide 4 includes core 41. Retaining member 5 retains optical waveguide 4 with at least a portion of core 41 being exposed.

Ferrule 71 is integrally joined to light emitting module M1 in such a manner as to retain an end portion of optical waveguide 4. Ferrule 71 positions core 41 with respect to light that is introduced into optical waveguide 4. Ferrule 71 (i.e., connecting member) is mechanically connectable to a connection target. Core 41 is configured so that light is introduced from an end thereof that faces the connection target.

In the present exemplary embodiment, the connection target is receptacle 81 provided for device body 2. Optical waveguide 4 includes light emitting portion 40. Light is applied from light emitting portion 40 to hair 91, whereby hair 91 is cut (see FIGS. 6A and 6B).

Device body 2 includes receptacle 81 (connection target), light source 21, optical system 22, and case 20. To receptacle 81 (connection target), ferrule 71 (connecting member) is mechanically connected. Light source 21 generates light that is to be introduced into core 41. Optical system 22 is disposed between light source 21 and receptacle 81 (connection target). Case 20 accommodates light source 21 and optical system 22.

When the light generated by light source 21 enters a tip end face (light receiving surface 40A: see FIG. 1) of optical waveguide 4 with hair cutting member 3 being attached to device body 2, the light propagates within optical waveguide 4. In the present exemplary embodiment, light source 21 is a laser light source, and the light that propagates within optical waveguide 4 is laser light.

In the present exemplary embodiment, the connecting member (ferrule 71) positions core 41 and also is mechanically connectable to a connection target (receptacle 81). Accordingly, when an installer attaches hair cutting member 3 onto device body 2 with the connecting member (ferrule 71) being connected to the connection target (receptacle 81), as illustrated in FIG. 1, the installer is allowed to save the trouble of checking the position of core 41.

The installer is able to easily attach the hair cutting member 3 to the connection target (receptacle 81), that is, device body 2, without paying close attention to the position of the optical axis of core 41. As a result, ease of assembly is improved for hair cutting member 3, device body 2, and hair cutting device 1.

Herein, the installer may be, for example, a worker who manufactures hair cutting device 1. The installer may be a user of hair cutting device 1 who replaces hair cutting member 3 due to deterioration over time or the like.

Figure 5:
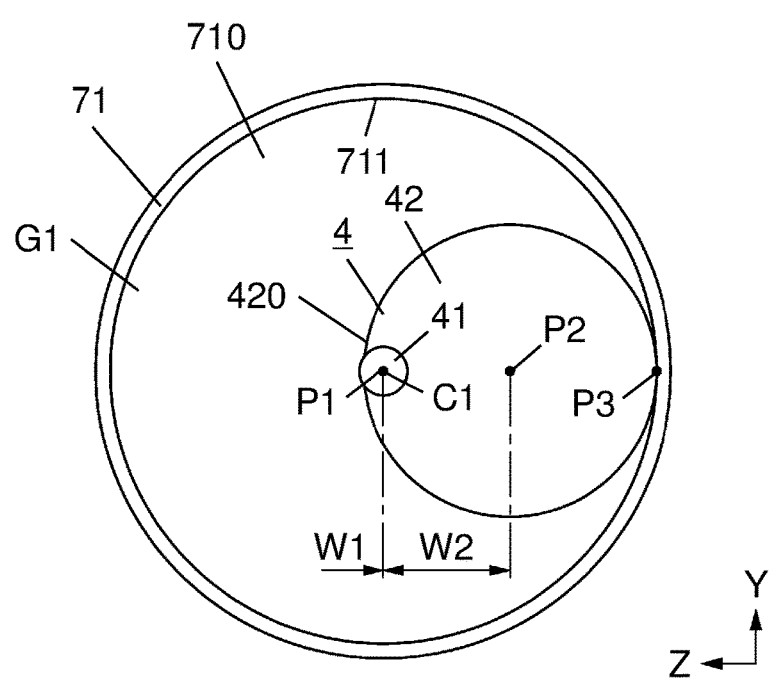
FIG. 5 is a plan view of an optical waveguide viewed from an end face of a ferrule of the hair cutting member according to the exemplary embodiment.

In the present exemplary embodiment, as illustrated in FIGS. 1, 2, and 5, hair cutting member 3 includes optical waveguide 4, a connecting member (ferrule 71), and bonding member G1.

Optical waveguide 4 includes core 41 and cladding 42 that covers at least a portion of core 41. Optical waveguide 4 guides light to hair 91 growing on skin 92 (see FIG. 6A). Bonding member G1 bonds optical waveguide 4 and the connecting member (ferrule 71) together. Core 41 is disposed off-center toward the outer circumference of cladding 42.

As illustrated in FIG. 5, first distance W1 is a distance between center P1 of end face 710 and optical axis C1 of core 41, viewed from end face 710 of the connecting member (ferrule 71). Second distance W2 is a distance between center P1 of end face 710 and center P2 of cladding 42. First distance W1 is shorter than second distance W2. In the present exemplary embodiment, center P1 is in agreement with optical axis C1 of core 41, so first distance W1 is zero (0).

In this configuration, core 41 is disposed off-center toward the outer circumference of cladding 42, and first distance W1 is shorter than second distance W2. This allows optical axis C1 of core 41 to be disposed closer toward the center of the connecting member (ferrule 71) easily. As a result, it is possible to adjust the optical system easily in hair cutting member 3 and hair cutting device 1.

2. Details

Hair cutting member 3 and hair cutting device 1 according to the present exemplary embodiment will be described with reference to FIGS. 1 to 10.

The present exemplary embodiment uses three axes (X-axis, Y-axis, and Z-axis) that are orthogonal to each other for explanation purposes. The X-axis is an axis extending along the longitudinal axis of optical waveguide 4. The Y-axis is an axis extending along a direction in which opening 31 of cover 30 of hair cutting member 3 faces skin 92. The Z-axis is an axis orthogonal to the X-axis and Y-axis.

2.1 Definitions

In the present disclosure, hair 91 means hair growing on skin 92, including various types of human body hair, such as head hair, facial hear, eyebrow, leg hair, nose hair, and ear hair. Hair 91 in the present disclosure may include hair of animals, such as dogs and cats, for example.

Hair cutting device 1 is a device for cutting these kinds of hairs 91. The term "skin" in the present disclosure means to include artificial skin. In the present exemplary embodiment, hair 91 that is to be cut by hair cutting device 1 may be facial hair growing on human facial skin 92, in particular.

In the present disclosure, cutting of hair 91 may include shaving of hair 91, cutting of hair 91 uniformly to a desired length, and cutting only the tip of hair, for example.

Accordingly, examples of the hair cutting device according to the present disclosure include shavers or hair shaving devices; which are devices used for shaving hair 91, as well as trimmers, hair clippers, or scissors, which are devices used for uniformly cutting hair to a desired length.

In the present disclosure, cutting of hair 91 means to include not only cutting hair 91 into two parts at a substantially planar cutting surface but also causing damages to a cut portion of hair 91 to split hair 91 at the cut portion. In the present exemplary embodiment, hair cutting device 1 is a shaver used for shaving hair 91 (facial hair) that is to be cut.

In the present disclosure, the term "laser" means light amplification by stimulated emission of radiation. An example of light source 21 that generates laser light is a semiconductor laser (laser diode) that makes use of recombination radiation of semiconductor.

Laser light exhibits higher performance in coherence, output power (power density), monochromaticity (single wavelength), and directivity than the light generated by a light emitting diode.

In the present disclosure, the optical waveguide is an optical member that guides light along a desired path. A specific example of the optical waveguide is an optical fiber. The optical fiber is an elongated fibrous substance that has a two-layer structure including a core, which is the central portion, and a cladding, which surrounds the core. Because the core has a higher refractive index than the cladding, the optical fiber enables light to propagate within the core with the light being confined within the core by total internal reflection.

Thereby, the optical fiber is able to guide light along a desired path. In the present exemplary embodiment, an optical waveguide means, not just a transmission path that allows communication light signals to propagate, but an optical member in general that is able to guide light along a desired path.

In the present disclosure, the term "retaining" means that one object supports another object while the two objects keep their relative positional relationship with each other. In other words, retaining member 5 may not firmly fix optical waveguide 4.

In the present disclosure, the refractive index is a value obtained by dividing the speed of light in vacuum by the speed of light (more precisely, phase velocity) in a medium. Basically, the refractive index is dependent on the substance. For example, the refractive index of air is 1.0003, and the refractive index of water is 1.3334. The refractive index may vary depending on the wavelength of the incident light, even for the same kind of substance. In the present disclosure, the refractive index is shown based on the light having a wavelength of 404.7 nm (mercury h-line).

In the present disclosure, power density means the light intensity per unit area (1 $cm^2$). The unit of power density is $kW/cm^2$ or $J/(scm^2)$. Even when there are variations of distribution of light intensity in a cross section of optical waveguide 4, it is possible to calculate an averaged power density over the entire cross section of core 41 by dividing the light intensity that passes through optical waveguide 4 by the cross-sectional area of core 41 of optical waveguide 4. In the present disclosure, the power density is calculated in this manner.

2.2 Overall Configuration

An overall configuration of hair cutting device 1 according to the present exemplary embodiment will be described below with reference to FIGS. 1, 2, 6A and 6B.

As described above, hair cutting device 1 includes hair cutting member 3 and device body 2. Hair cutting member 3 includes light emitting module M1 and ferrule 71, which is the connecting member. Hair cutting member 3 further includes holder H1, securing member F1, bonding member G1, cover 30, and securing cap 34. At least a portion of light emitting module M1 and at least a portion of ferrule 71 are each inserted into holder H1.

Light emitting module M1 includes optical waveguide 4 and retaining member 5. Retaining member 5 retains optical waveguide 4 with at least a portion of later-described core 41 of optical waveguide 4 being exposed. Light emitting module M1 further includes securing block 32.

Device body 2 includes receptacle 81 (connection target) to which ferrule 71 of hair cutting member 3 is mechanically connected, light source 21, optical system 22, and case 20. Light source 21 generates light that is to be introduced into core 41. Optical system 22 is disposed between light source 21 and receptacle 81. Case 20 accommodates light source 21 and optical system 22.

Figure 6B:
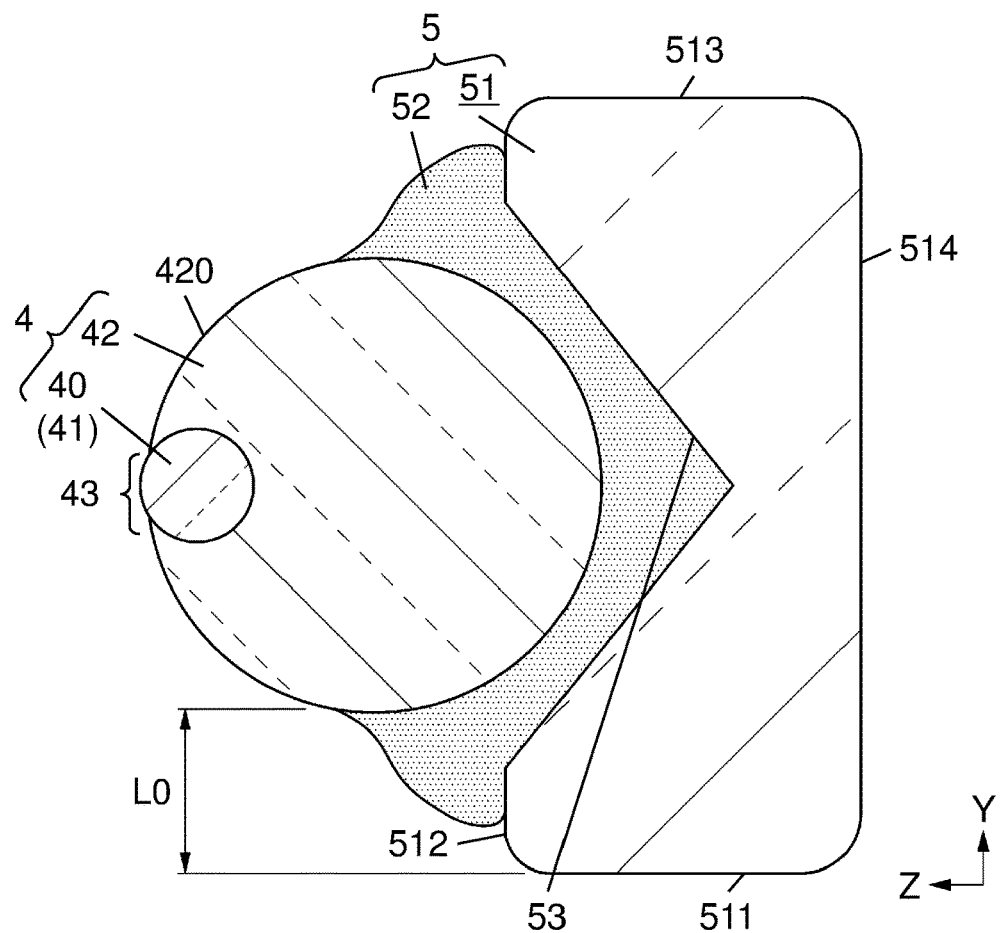
FIG. 6B is an enlarged view illustrating a major part of FIG. 6A.

Optical waveguide 4 includes light emitting portion 40 (see FIGS. 6A and 6B). Optical waveguide 4 causes the light generated by light source 21 to propagate within the interior thereof and outputs the light from light emitting portion 40. Hair cutting device 1 applies the light emitted from light emitting portion 40 to hair 91 to thereby cut hair 91.

More specifically, in the present exemplary embodiment, the refractive index of light emitting portion 40 is set to be a value close to the refractive index of hair 91 that is to be cut. As a result, when hair 91 comes into contact with light emitting portion 40, light leaks out of light emitting portion 40 toward hair 91, and by the energy of the light, hair 91 is cut.

When hair 91 is not in contact with light emitting portion 40, the amount of the light that leaks out of light emitting portion 40 is reduced due to the difference between the refractive index of the air (=1.0) that is in contact with light emitting portion 40 and the refractive index of light emitting portion 40.

In the present exemplary embodiment, hair cutting member 3 corresponds to the head of hair cutting device 1, and device body 2 corresponds to the grip of hair cutting device 1. Case 20 of device body 2 has, for example, an elongated prismatic shape having a central axis extending along the X-axis.

Hair cutting member 3 has an elongated cylindrical shape having a central axis extending along the X-axis. As illustrated in FIGS. 1 and 2, cover 30 of hair cutting member 3 accommodates light emitting module M1. Case 30 has, for example, an elongated prismatic shape having a central axis extending along the X-axis.

In the present exemplary embodiment, one end (ferrule 71) of the longitudinal axis of hair cutting member 3 is connected to receptacle 81, which is located at one end of the longitudinal axis of case 20. This configuration allows hair cutting device 1 as a whole to have an elongated substantially I shaped external appearance having a central axis extending along the X-axis.

In other words, hair cutting device 1 as a whole has a rod shape. The rod shape is such a shape that the central axis of cylindrical-shaped hair cutting member 3 is in agreement with the central axis of prismatic-shaped case 20 when ferrule 71 is joined to receptacle 81. Both case 20 and cover 30 are made of synthetic resin in the present exemplary embodiment.

Thus, hair cutting device 1 as a whole has a substantially I shaped external appearance, and is used in the same manner as a straight blade razor is used.

Specifically, the user grips case 20 to holds hair cutting device 1. The user presses the head of hair cutting device 1, that is, a side surface of cylindrical shaped hair cutting member 3, against skin 92 of the user, and moves hair cutting member 3 along skin 92 in the positive direction of the Z-axis. At this time, hair cutting device 1 cuts hair 91 located in the moving direction of hair cutting member 3 (that is, the positive direction of the Z-axis).

Hair cutting device 1 may have a shape other than a rod shape. For example, device body 2 may be pivotably supported in the vicinity of receptacle 81 so as to be pivotable within a predetermined range of angles. This configuration allows the shape of hair cutting device 1 as a whole to change from a substantially I shaped form to a substantially L shaped form. The user is able to use hair cutting device 1 in both substantially I shaped form and substantially L shaped form.

In addition to receptacle 81, light source 21, optical system 22, and case 20, device body 2 further includes control circuit 6, battery 23, fan 24, heat sink 25, and operation portion 26.

All of control circuit 6, optical system 22, battery 23, fan 24, and heat sink 25 are accommodated inside case 20. Operation portion 26 is disposed on a surface of case 20 that is on the negative side of the Y-axis. Hair cutting member 3 includes optical waveguide 4. By connecting one end that is on the light receiving surface 40A side (see FIG. 1) of optical waveguide 4 to receptacle 81, optical waveguide 4, as well as ferrule 71, is disposed so as to oppose optical system 22 inside case 20.

Light source 21 converts electrical energy into optical energy to generate light. In the present exemplary embodiment, light source 21 is a laser light source, and the light generated by light source 21 is laser light produced by stimulated emission. Light source 21 is constructed of a semiconductor laser that makes use of recombination radiation of semiconductor.

Light source 21 generates a laser light having a peak wavelength or a dominant wavelength that is longer than 400 nm. The wavelength of the light generated by light source 21 is less than or equal to 700 nm.

It is expected that light having a wavelength within a range of 400 nm to 450 nm has a bactericidal effect against the bacteria existing on skin 92, such as *Cutibacterium acnes*. It is expected that light having a wavelength within a range of 450 nm to 700 nm has an activating effect on skin 92.

Control circuit 6 is a circuit that controls at least light source 21. Control circuit 6 supplies electric power to light source 21 to operate light source 21. Control circuit 6 turns on/off light source 21 and adjusts the outputs (brightness, wavelength, and so forth) of light source 21.

Control circuit 6 includes a printed circuit board (substrate) and a plurality of electronic components mounted on the printed circuit board. Control circuit 6 controls fan 24 and operation portion 26, in addition to light source 21. More details on control circuit 6 are described in section "2.6 Control Circuit" below.

Optical system 22 includes a plurality of lenses disposed between light source 21 and receptacle 81. Optical system 22 guides the light emitted from light source 21 to optical waveguide 4. In the example shown in FIG. 2, optical system 22 includes first lens 221, second lens 222, third lens 223, and fourth lens 224. It should be noted, however, that FIG. 2 is a merely schematic representation of optical system 22 and does not accurately depict the shapes and arrangements of the lenses included in optical system 22.

Battery 23 supplies electric power to control circuit 6, light source 21, and fan 24. In the present exemplary embodiment, battery 23 is a secondary battery, such as a lithium ion battery.

Fan 24 cools light source 21. Specifically, fan 24 produces an air stream that hits heat sink 25 inside case 20 to facilitate the heat dissipation caused by heat sink 25.

Heat sink 25 is composed of a material that has a relatively high thermal conductivity, such as aluminum, for example. Heat sink 25 is thermally coupled to light source 21 to mainly dissipate the heat of light source 21.

Operation portion 26 accepts user operations, and outputs information corresponding to the user operations to control circuit 6. In the present exemplary embodiment, operation portion 26 includes at least one mechanical switch, such as a push switch and a slide switch.

Opening 31 (see FIG. 3) is formed in a surface of cover 30 that comes into contact with skin 92 of the user (that is, the surface thereof that is on the negative side of the Y-axis). Opening 31 has an elongated rectangular shape having a central axis extending along the X-axis. Opening 31 allows at least light emitting portion 40 to be exposed outside of cover 30. Through opening 31, the interior space of cover 30 is allowed to communicate with the outside environment.

Cover 30 accommodates a portion of optical waveguide 4, retaining member 5, and securing block 32. When hair cutting member 3 is attached to device body 2, light receiving surface 40A of optical waveguide 4 is opposed in close proximity to fourth lens 224 of optical system 22 within case 20 of device body 2.

In this condition, optical waveguide 4 is optically coupled to light source 21 via optical system 22. In the present exemplary embodiment, opening 31 allows retaining member 5 and securing block 32, as well as light emitting portion 40 of optical waveguide 4, to be exposed outside of cover 30.

Optical waveguide 4 allows the light generated by light source 21 to propagate therethrough, and guides the light along a desired path. In the present exemplary embodiment, optical waveguide 4 is an optical fiber including core 41 and cladding 42. Cladding 42 covers at least a portion (a portion in the present exemplary embodiment) of core 41.

Core 41 is disposed off-center toward the outer circumference of cladding 42. As illustrated in FIGS. 5 and 6B, core 41 is disposed so as to be in contact with outer circumferential surface 420 of cladding 42, and a portion of core 41 is exposed from outer circumferential surface 420 of cladding 42, in the present exemplary embodiment.

Core 41 is disposed off-center in such a manner that a portion of the outer circumference of core 41 protrudes outward from outer circumferential surface 420 of cladding 42, in a region extending from one end face (i.e., light receiving surface 40A) to the other end face (terminal end surface 40B) of optical waveguide 4 along the X-axis direction.

Hereinafter, a region of core 41 that protrudes outward from outer circumferential surface 420 of cladding 42 is referred to as "protruding region 43" (see FIG. 6B). Light emitting portion 40 of optical waveguide 4 corresponds to a region of protruding region 43 (see FIG. 2), which is formed extending from light receiving surface 40A to terminal end surface 40B, that is within the area exposed from opening 31.

Optical waveguide 4 may further include a protective sheath, which is a resin covering member that protects cladding 42. In other words, optical waveguide 4 may be an optical fiber having a three-layer structure including core 41, cladding 42, and additionally, a protective sheath covering the outside of cladding 42.

However, in at least a portion of optical waveguide 4 that is exposed from opening 31, it is preferable that the protective sheath be removed so as to expose core 41 and cladding 42.

Retaining member 5 is a member that retains optical waveguide 4. In the present exemplary embodiment, retaining member 5 makes contact with and retains a portion of optical waveguide 4 along the longitudinal axis thereof. Hereinbelow, for illustrative purposes, optical waveguide 4 is divided three regions (first region 401, second region 402, and third region 403) along the X-axis, as shown in FIG. 2.

As illustrated in FIG. 2, retaining member 5 retains first region 401 of optical waveguide 4. Light emitting portion 40 is disposed within first region 401.

Second region 402 and third region 403 of optical waveguide 4 protrude from retaining member 5 in the positive direction of the X-axis. Third region 403 is secured within ferrule 71 by bonding member G1. Third region 403 is positioned by ferrule 71.

Second region 402 is a region between first region 401 and third region 403, which is interposed between retaining member 5 and ferrule 71. Optical waveguide 4 is bent in second region 402. Second region 402 is secured within holder H1 by securing member F1. That is, first region 401 and third region 403 are arranged so as to be staggered from each other along the Y-axis.

More specifically, core 41 includes optical axis C2 in first region 401 and optical axis C1 in third region 403. Optical axis C1 is positioned by ferrule 71 and is non-coaxial with optical axis C2 of light emitting module M1.

Retaining member 5 is secured to securing block 32. Retaining member 5 may be secured to securing block 32 using, as appropriate, various techniques of bonding, such as adhesive bonding, melt bonding, gluing, and coupling using fastening members (for example, screws). As a result, optical waveguide 4 (first region 401) is indirectly secured to securing block 32 via retaining member 5.

Securing block 32 is secured to cover 30. Securing block 32 may be made of either synthetic resin or metal. Securing block 32 has an elongated prismatic shape having a central axis extending along the X-axis. Securing block 32 may be secured to cover 30 using, as appropriate, various techniques of bonding, such as adhesive bonding, melt bonding, gluing, and coupling using fastening members (for example, screws).

Retaining member 5 is secured to securing block 32, as described above. This means that optical waveguide 4 (first region 401) is indirectly secured to cover 30 via retaining member 5 and securing block 32.

In hair cutting member 3, all of light emitting portion 40 of optical waveguide 4, retaining member 5, and securing block 32 are exposed to the outside of cover 30 through opening 31. Specifically, as illustrated in FIGS. 1 and 2, securing block 32 is disposed along the longitudinal axis (along the X-axis) of opening 31 of cover 30.

Retaining member 5 is secured to the surface of securing block 32 that faces in the moving direction of hair cutting device 1 (facing the negative side of the Z-axis). Furthermore, with respect to the shorter axis direction (i.e., the Z-axis direction) of opening 31, securing block 32 and retaining member 5 are disposed toward the opposite side to the moving direction of hair cutting device 1 (that is, the positive side of the Z-axis). Thus, it is ensured that a clearance gap is provided in the moving direction of hair cutting device 1 (hair cutting member 3).

Securing block 32 and retaining member 5 are disposed so that their surfaces that are on the negative side of the Y-axis are flush with the surface of the cover 30 that is on the negative side of the Y-axis. As illustrated in FIG. 6A, optical waveguide 4 (light emitting portion 40) is secured to the surface of retaining member 5 that faces in the moving direction of hair cutting device 1 (i.e., that is on the positive side of the Z-axis).

Although not shown in FIGS. 1 and 2, hair cutting device 1 may further include, for example, a charging circuit for battery 23, a display unit for indicating the operation status of hair cutting device 1, and the like.

2.3 Hair Cutting Member

2.3.1 Configuration of Hair Cutting Member

Next, more details of the configuration of hair cutting member 3 according to the present exemplary embodiment will be described below with reference to FIGS. 1 to 6B.

Figure 3:
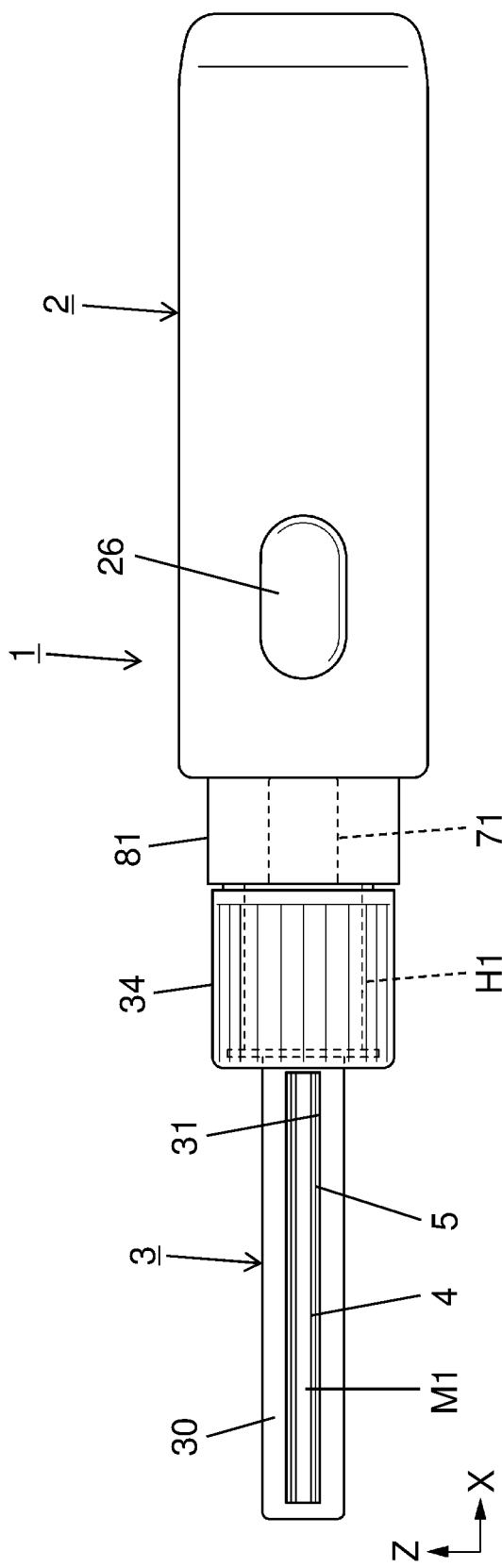
FIG. 3 is a front view of the hair cutting device according to the exemplary embodiment.
Figure 4:
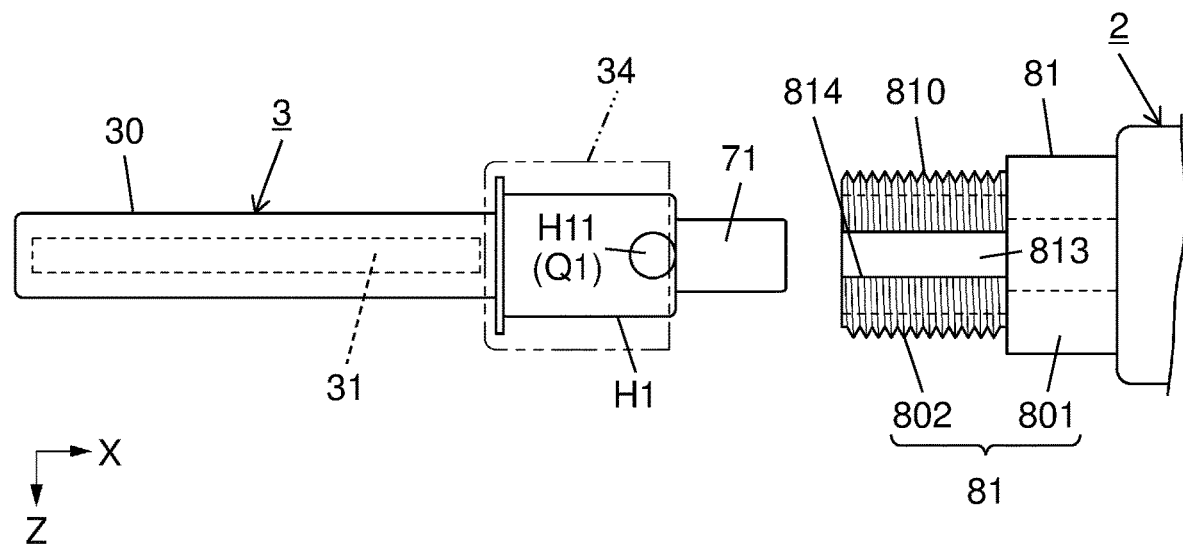
FIG. 4 is a rear view illustrating a major part of the hair cutting device according to the exemplary embodiment, showing a state in which the hair cutting member is detached from the device body.

FIG. 3 is a front view of hair cutting device 1 viewed in the positive direction from the negative side of the Y-axis. FIG. 4 is a rear view of hair cutting device 1 viewed in the negative direction from the positive side of the Y-axis, in a state in which hair cutting member 3 is detached from receptacle 81 of device body 2.

FIG. 5 is a plan view of optical waveguide 4, ferrule 71, and bonding member G1, viewed from end face 710 of ferrule 71 of hair cutting member 3. FIG. 6A is a schematic cross-sectional view illustrating a peripheral structure of optical waveguide 4 and retaining member 5 of hair cutting member 3. FIG. 6B is an enlarged view illustrating a major part of FIG. 6A.

As described previously, hair cutting member 3 according to the exemplary embodiment includes light emitting module M1, ferrule 71, holder H1, securing member F1, bonding member G1, cover 30, and securing cap 34. Cover 30 and securing cap 34 are not essential components of hair cutting member 3 and may therefore be eliminated.

Light emitting module M1 includes optical waveguide 4, retaining member 5, and securing block 32. In particular, optical waveguide 4 guides light to hair 91 growing on skin 92.

2.3.2 Optical Waveguide

Optical waveguide 4 of light emitting module M1 includes light emitting portion 40, as described previously. In the present exemplary embodiment, optical waveguide 4 is an optical fiber including core 41 and cladding 42.

For example, both core 41 and cladding 42 may be made of synthetic quartz. For example, core 41 may be made of pure synthetic quartz, and cladding 42 may be made of synthetic quartz in which an impurity is added so that cladding 42 shows a different refractive index from core 41.

In the present exemplary embodiment, when the fiber incident NA (Numerical Aperture) is 0.1, the refractive index of core 41 is 1.4698, and the refractive index of cladding 42 is 1.4309. When the fiber incident NA is 0.2, the refractive index of core 41 is 1.4698, and the refractive index of cladding 42 is 1.309. These numerical values of fiber incident NA and refractive index are merely exemplary and are not intended to specify the difference in refractive index between core 41 and cladding 42.

As illustrated in FIG. 5, core 41 is disposed off-center toward the outer circumference of cladding 42. In other words, optical axes C1 and C2 of core 41 are offset from center P2 of cladding 42. As illustrated in FIG. 5, core 41 and cladding 42 are each in a circular shape when viewed from light receiving surface 40A.

In the present exemplary embodiment, optical axes C1 and C2 of core 41 are coaxial with the central axis of core 41. Core 41 may be formed in a D shape viewed from light receiving surface 40A by cutting an outer circumferential portion of core 41. In that case, optical axes C1 and C2 of core 41 may be in agreement with the center of gravity of core 41. Light receiving surface 40A is flush with end face 710 of ferrule 71.

In the present exemplary embodiment, the diameter of core 41 is about 10 μm, and the diameter of cladding 42 is about 50 μm to about 125 μm. However, the present disclosure is not limited by these numerical values.

Core 41 is disposed in an outer circumferential portion of cladding 42 so that a portion of core 41 (i.e., protruding region 43) is exposed from the outer circumferential portion. Protruding region 43 is provided extending from light receiving surface 40A to terminal end surface 40B. Accordingly, hair cutting member 3 has a configuration such that the light passing through optical waveguide 4 easily leaks to the outside through protruding region 43.

Light emitting portion 40 of optical waveguide 4 approximately corresponds to a region of protruding region 43 that is within the area exposed from opening 31 along the X-axis (see FIG. 2).

More precisely, because light does not leak from the portion of optical waveguide 4 that is covered by retaining member 5, this portion does not function as light emitting portion 40. In the present exemplary embodiment, light emitting portion 40 is a portion of core 41 that is exposed without being covered by cladding 42, and also without being covered by holder H1 or ferrule 71.

FIGS. 6A, 6B, and so forth each show a cross section of retaining member 5 and optical waveguide 4 including light emitting portion 40 along a Y-Z plane.

In the present exemplary embodiment, the refractive index of light emitting portion 40 of optical waveguide 4 is lower than the refractive index of surface 921 of skin 92 (see FIG. 6A). Human skin 92 includes an epidermis, a dermis, and a subcutaneous tissue. Surface 921 of skin 92 means the epidermis or the surface thereof that is disposed to be the outermost one of a plurality of elements that constitute skin 92.

In the present exemplary embodiment, light emitting portion 40 is composed of core 41 of optical waveguide 4, which includes core 41 and cladding 42. The refractive index of core 41 is set to be lower than the refractive index of surface 921 of skin 92.

For example, it is assumed that the refractive index of surface 921 of human skin 92 is 1.4770. In this case, it is possible to satisfy the condition that the refractive index of light emitting portion 40 is lower than the refractive index of surface 921 of skin 92 when the refractive index of core 41, which is light emitting portion 40, is 1.4698, as described above.

More specifically, the refractive index of light emitting portion 40 is less than or equal to 1.47 in the present exemplary embodiment. The refractive index of light emitting portion 40 is set at less than or equal to 1.4700 so that the refractive index of light emitting portion 40 becomes lower than the refractive index of surface 921 of skin 92.

This enables the refractive index of light emitting portion 40 to be lower than the refractive index of surface 921 of skin 92 even when there is some variation in the refractive index of surface 921 of skin 92. That is, it is possible to satisfy the condition that the refractive index of light emitting portion 40 is lower than the refractive index of surface 921 of skin 92, even when the refractive index of surface 921 of skin 92 is slightly lower than 1.4770.

When the refractive index is compared between surface 921 of skin 92, hair 91, and light emitting portion 40 (core 41), hair 91 shows the highest refractive index, followed by surface 921 of skin 92, and light emitting portion 40 is the lowest.

For example, it is assumed that the refractive index of human hair 91 (facial hair), which is to be cut by hair cutting device 1, is 1.5432. In this case, it is possible to satisfy the condition that the refractive index of light emitting portion 40 is lower than the refractive index of surface 91 of skin 92 when the refractive index of surface 921 of skin 92 is 1.4770.

In the present exemplary embodiment, because the refractive index of light emitting portion 40 is lower than that of hair 91, light leaks out of light emitting portion 40 toward hair 91 when light emitting portion 40 comes into contact with hair 91. Hair 91 is cut by the energy of the light. The principle of how hair 91 is cut will be described in detail in section "2.4. Usage Example" below.

In the state where light emitting portion 40 is not in contact with hair 91 but it is in contact with only the air, the leakage of light from light emitting portion 40 is reduced because of the difference in refractive index between light emitting portion 40 and the air.

It is desirable that the refractive index difference between surface 921 of skin 92 and hair 91 and the refractive index difference between hair 91 and light emitting portion 40 be as small as possible while maintaining the magnitude relationship of the refractive indices. In that case, light easily leaks out from light emitting portion 40 to hair 91 when hair 91 comes into contact with light emitting portion 40.

In the present exemplary embodiment, the refractive index of light emitting portion 40 (core 41) is 1.4698, the refractive index of surface 921 of skin 92 is 1.4770, and the refractive index of hair 91 is 1.5432. The refractive index of light emitting portion 40 and the refractive index of surface 921 of skin 92 are substantially the same. The phrase "two refractive indices are substantially the same" means that two refractive indices are in a close range such that the lower one of the two different refractive indices is within the range ±5% of the higher one.

In this case, for example, when the incident angle of light is assumed to be 80 degrees, the reflectivity (s-polarized light) at the interface between an object having a refractive index of −5% of the refractive index of hair 91 and an object having the same refractive index as that of hair 91 is 13.2%. The reflectivity (s-polarized light) at the interface between light emitting portion 40 and hair 91 is 12.5%, and the reflectivity (s-polarized light) at the interface between skin 92 and hair 91 is 11.3%. The incident angle of light means an angle between the light and the normal line of surface 921 of skin 92. When the incident angle of light is 80 degrees, the fiber incident NA is about 0.17.

Thus, even when the refractive index changes by −5%, the reflectivity changes only by 2%. In the present exemplary embodiment, the refractive index of light emitting portion 40 (1.4698) and the refractive index of surface 921 of skin 92 are within the range ±5% of the refractive index of hair 91 (1.5432). Therefore, it can be said that these are substantially the same.

As already discussed in section "2.1 Definitions", the refractive index may vary depending on the wavelength even for the same kind of substance. The above-described relationship of the refractive indices is invariant at least within the wavelength range of the light that is generated by light source 21. That is, at least when the wavelength of the light generated by light source 21 is from 400 nm to 700 nm, for example, the magnitude relationship of the refractive indices is invariant between surface 921 of skin 92, hair 91, and light emitting portion 40.

The refractive index of cladding 42 is lower than the refractive index of light emitting portion 40 (core 41). That is, among core 41, cladding 42, surface 921 of skin 92, and hair 91, cladding 42 has the lowest refractive index.

In the present exemplary embodiment, the power density of the light that is propagated by optical waveguide 4 is higher than or equal to 50 kW/cm$^2$ at least at the time of cutting hair 91. In other words, when optical waveguide 4 propagates light, the light intensity per unit area (1 cm$^2$) of a cross section of core 41 is higher than or equal to 50 kW. The power density of the light passing through optical waveguide 4 should be higher than or equal to 50 kW/cm$^2$ at least at the time of cutting hair 91, but need not always be higher than or equal to 50 kW/cm$^2$.

In the present exemplary embodiment, the power density of the light passing through optical waveguide 4 at the time of cutting hair 91 is from 50 kW/cm$^2$ to 300 kW/cm$^2$. It is preferable that the power density of the light passing through optical waveguide 4 at the time of cutting hair 91 be higher than or equal to 70 kW/cm$^2$, at which it is possible to cut hair 91, and more preferably higher than or equal to 75 kW/cm$^2$.

In order to cut hair 91 quickly (for example, within about 0.1 sec.), it is more preferable that the power density of the light passing through optical waveguide 4 at the time of cutting hair 91 be higher than or equal to 100 kW/cm$^2$.

Taking into consideration the output power of the laser and the diameter of the optical fiber that are available as commercial products, it is preferable that the power density of the light passing through optical waveguide 4 at the time of cutting hair 91 be less than or equal to 200 kW/cm$^2$. In the present exemplary embodiment, the initial value of the power density of the light passing through optical waveguide 4 at the time of cutting hair 91 is set at 100 kW/cm$^2$.

Although the details will be described in section "2.4. Usage Example" and section "3. Operation" below, hair cutting device 1 is able to efficiently cut hair 91 when light emitting portion 40 emits the light that has such a level of power density described above.

In the present exemplary embodiment, the power density of the light passing through optical waveguide 4 is variable. The power density of the light passing through optical waveguide 4 may be variable either continuously or in a step-by-step manner.

In the present exemplary embodiment, the power density of the light passing through optical waveguide 4 is adjusted by adjusting the output power from light source 21. The term "adjusting" of the power density herein is meant to include both an embodiment in which the power density is fixed to a predetermined value and an embodiment in which the power density is changed from an initial value.

Specifically, when the power density of the light passing through optical waveguide 4 is fixed to an initial value, the output power of light source 21 is determined so that the power density is initially 100 kW/cm$^2$. When the power density of the light passing through optical waveguide 4 is changed from the initial value, the output power of light source 21 is determined so that the power density changes and thereafter results in a desired value. The configuration for determining the output power from light source 21 will be described in section "2.6 Control Circuit" below.

2.3.3 Retaining Member

Retaining member 5 (retaining structure) of light emitting module M1 is described below with reference to FIGS. 6A and 6B.

As illustrated in FIGS. 6A and 6B, retaining member 5 retains optical waveguide 4 so that a portion of core 41 (i.e., protruding region 43) is exposed. In other words, optical waveguide 4 is retained so that the light leakage from protruding region 43 of core 41 is not hindered by retaining member 5.

Specifically, optical waveguide 4 is retained by retaining member 5 so that at least light emitting portion 40 is exposed from the surface of retaining member 5 that faces in the moving direction of hair cutting device 1 (i.e., that is on the positive side of the Z-axis). In other words, optical waveguide 4 is retained by retaining member 5 so that protruding region 43 faces in the positive direction of the Z-axis.

Protruding region 43 of optical waveguide 4 retained in this manner functions as light emitting portion 40 that cuts hair 91 by applying light to hair 91. In the present exemplary embodiment, optical waveguide 4 is formed so that protruding region 43 faces in the positive direction of the Z-axis both inside holder H1 and inside ferrule 71.

Retaining member 5 is secured to securing block 32, and optical waveguide 4 (light emitting portion 40) is indirectly secured to cover 30 via retaining member 5 and securing block 32.

Light emitting portion 40, retaining member 5, and securing block 32 are exposed to the outside of cover 30 through opening 31. With respect to the shorter axis direction (i.e., the Z-axis direction) of opening 31, securing block 32 and retaining member 5 are disposed off-center toward the opposite side to the moving direction of hair cutting device 1 (i.e., toward the negative side of the Z-axis) in opening 31.

This makes it possible to introduce hair 91, which is to be cut, into a gap between the circumferential edge of opening 31 and the surface of retaining member 5 on which optical waveguide 4 is retained so as to expose light emitting portion 40, that is, the surface thereof that faces in the moving direction of hair cutting device 1 (i.e., that is on the positive side of the Z-axis) (see FIG. 6A).

With the above-described configuration, hair 91 is introduced into cover 30 through opening 31 so as to oppose light emitting portion 40 retained by retaining member 5, and is brought into contact with light emitting portion 40, as illustrated in FIG. 6A.

In the present exemplary embodiment, retaining member 5 includes base 51 and bonding member 52. Bonding member 52 bonds optical waveguide 4 to base 51. Base 51 and bonding member 52 are both made of synthetic resin that has light transmissivity. Base 51 is a molded resin product that is formed using a mold. Bonding member 52 is a cured substance of a paste-type resin adhesive agent.

For example, a portion of optical waveguide 4 is buried in paste-type bonding member 52 applied on base 51, and thereafter bonding member 52 is cured. This enables optical waveguide 4 to be bonded onto base 51 by bonding member 52 and allows a portion of optical waveguide 4 to be exposed from bonding member 52. Thus, retaining member 5 retains optical waveguide 4 so that light emitting portion 40 is exposed from one surface of retaining member 5.

Base 51 has an elongated prismatic shape having a central axis extending along the X-axis. Base 51 may be secured to a surface of securing block 32 that faces in the moving direction of hair cutting device 1 (i.e., that is on the positive side of the Z-axis) using, as appropriate, various techniques of bonding, such as adhesive bonding, melt bonding, gluing, and coupling using fastening members (for example, screws). In the present exemplary embodiment, the refractive index of base 51 is higher than or equal to the refractive index of core 41 (light emitting portion 40).

As illustrated in FIG. 6B, base 51 includes opposing surface 511, side surface 512, back surface 513, and reverse surface 514. The cross section of base 51 that is orthogonal to its longitudinal axis (the X-axis) has a substantially rectangular shape having line segments on these four surfaces.

Opposing surface 511 opposes surface 921 of skin 92 at the time of cutting hair 91. Side surface 512 opposes hair 91 at the time of cutting hair 91. Back surface 513 faces the opposite side of opposing surface 511. Reverse surface 514 faces the opposite side of side surface 512. Optical waveguide 4 is retained on side surface 512.

Bonding member 52 bonds optical waveguide 4 to base 51. In the present exemplary embodiment, optical waveguide 4 is joined to base 51 by bonding member 52 applied on side surface 512 of base 51 and is retained on side surface 512 of base 51.

Bonding member 52 is coated on the base 51 across the entire longitudinal axis (X-axis) of base 51.

Bonding member 52 is a cured substance of a paste-type resin adhesive agent, so it is difficult to completely control the shape of bonding member 52. However, the shape of bonding member 52 may be adjustable to some extent by, for example, adjusting the amount of bonding member 52 or the like.

In the present exemplary embodiment, as illustrated in FIG. 6B, the shape of bonding member 52 is adjusted to expose protruding region 43 from bonding member 52 while burying a portion of cladding 42 in bonding member 52 in a cross section that is orthogonal to the longitudinal axis (the X-axis) of base 51.

In more detail, bonding member 52 bulges upward along the circumferential surface of cladding 42 up to the height of center P2 (see FIG. 5) of cladding 42 with respect to the moving direction of hair cutting device 1 (the Z-axis direction) due to the wettability of cladding 42. Thereby, approximately half of the circumferential surface of cladding 42 is covered by bonding member 52, and protruding region 43 and approximately half of the circumferential surface of cladding 42 are exposed from retaining member 5 (bonding member 52).

In the present exemplary embodiment, bonding member 52 is directly in contact with cladding 42 of light emitting portion 40. For this reason, bonding member 52 is unlikely to be affected in selecting the type of the material due to the refractive index.

That is, as long as the refractive index of light emitting portion 40 (core 41) is 1.4698, the refractive index of bonding member 52 may be higher than 1.4698. Cladding 42 having a lower refractive index than that of light emitting portion 40 is interposed between light emitting portion 40 and bonding member 52.

Therefore, even when the refractive index of bonding member 52 is higher than that of light emitting portion 40, cladding 42 is able to limit the leakage of light to an appropriate level. As a result, it is possible to prevent the decrease of the power density of light that is caused by unnecessary leakage of light from core 41. The refractive index of bonding member 52 may be substantially equal to the refractive index of light emitting portion 40, or may be lower than the refractive index of light emitting portion 40.

Positioner 53 that positions optical waveguide 4 is formed on side surface 512 of base 51 on which optical waveguide 4 is retained. As illustrated in FIG. 6B, positioner 53 is a groove formed in side surface 512 of b. Positioner 53 is formed across the entire longitudinal axis (X-axis) of base 51.

Cladding 42 is accommodated in positioner 53 and is retained on side surface 512 of base 51. In the present exemplary embodiment, positioner 53 is a groove having a V shaped cross section the depth of which is deeper toward the center of the shorter axis (width axis) of base 51. Optical waveguide 4 is placed substantially at the center of the shorter axis (width axis) of positioner 53 due to self-alignment effect.

Hair cutting member 3 includes a contact surface that comes into contact with skin 92 at the time of cutting hair 91. Optical waveguide 4 is retained by retaining member 5 so that height L0 (see FIG. 6B) from the contact surface is less than or equal to 100 μm. The contact surface corresponds to opposing surface 511 of base 51, the surface of securing block 32 that is on the negative side of the Y-axis, and the surface of cover 30 that is on the negative side of Y-axis.

Height L0 of optical waveguide 4 from such a contact surface is equal to the height of optical waveguide 4 from surface 921 of skin 92 at the time of cutting hair 91. Height L0 of optical waveguide 4 from the contact surface is set to less than or equal to 100 μm, and the distance (height) from surface 921 of skin 92 to optical waveguide 4 at the time of cutting hair 91 becomes less than or equal to 100 μm. It should be noted, however, that height L0 of optical waveguide 4 from the contact surface is greater than or equal to 1 μm, and is not zero (0).

In other words, optical waveguide 4 is detached from surface 921 of skin 92 at the time of cutting hair 91 by height L0 from the contact surface (opposing surface 511). As a result, even when there is a raised object, such as a pimple, on surface 921 of skin 92, for example, optical waveguide 4 is unlikely to be caught by the raised object.

2.3.4 Cover and Securing Cap

As already described above, cover 30 is made of synthetic resin, and cover 30 as a whole has an elongated prismatic shape having a central axis extending along the X-axis. Cover 30 is hollow, and includes opening 31. Cover 30 accommodates light emitting module M1 so as to expose light emitting portion 40 of optical waveguide 4 through opening 31.

Cover 30 accommodates a portion of light emitting module M1 that protrudes from holder H1 in the negative direction of the X-axis. Securing block 32 of light emitting module M1 is secured to cover 30.

Cover 30 includes insertion opening 300 (see FIG. 2) at its end face that faces in the positive direction of the X-axis. Light emitting module M1 is inserted from insertion opening 300 and is accommodated in cover 30. Cover 30 includes flange portion 301 at the circumferential edge of insertion opening 300.

Securing cap 34 is made of, for example, metal. Securing cap 34 may be made of synthetic resin. Securing cap 34 has a cylindrical shape having a central axis extending along the X-axis.

Securing cap 34 has an opening at its end face that is on the positive side of the X-axis, and has hole 340 (see FIG. 1) at its end face that is on the negative side of the X-axis. Cover 30 can be inserted through hole 340. The inner circumferential surface of securing cap 34 includes screw thread 341 to which screw part 810 of receptacle 81 is screw-fittable.

Cover 30 is secured to holder H1 via flange portion 301. When securing member F1 inside holder H1 is bonded to flange portion 301, cover 30 is secured to holder H1 with light emitting module M1 being accommodated therein.

When cover 30 is passed through hole 340 and securing cap 34 is moved in the positive direction of the X-axis, securing cap 34 is placed so as to cover holder H1. Flange portion 301 of cover 30, which makes contact with the inner circumferential portion of hole 340, restrains securing cap 34 from further moving in the positive direction of the X-axis. That is, the inner diameter of hole 340 is smaller than the outer diameter of flange portion 301. In the state shown in FIG. 2, securing cap 34 is rotatable relative to cover 30 and holder H1.

In the present exemplary embodiment, securing cap 34 has a restraining structure U1 (see FIG. 2) that restrains ferrule 71 from detaching from receptacle 81. Screw thread 341 of securing cap 34 corresponds to restraining structure U1.

Screw part 810 provided on receptacle 81 of device body 2 is screw-fitted to screw thread 341 of securing cap 34, whereby ferrule 71 is prevented from detaching from receptacle 81. This reduces the possibility of detachment of hair cutting member 3 from device body 2.

2.3.5 Ferrule

Ferrule 71 is a connecting member that is integrally joined to light emitting module M1 so as to retain an end portion of optical waveguide 4 (end portion on the light receiving surface 40A side). Ferrule 71 positions core 41 with respect to light that is introduced into optical waveguide 4.

Ferrule 71 is mechanically connectable to receptacle 81. When ferrule 71 is connected to receptacle 81, light is introduced into core 41 from its end facing receptacle 81. This light is emitted in the negative direction of the X-axis from light source 21 via optical system 22.

As illustrated in FIGS. 1 to 5, ferrule 71 is a member that has an elongated cylindrical shape having a central axis extending along the X-axis. Ferrule 71 has respective openings at both end faces of the X-axis. Ferrule 71 is formed of, for example, a sintered ceramic material, such as zirconia. Ferrule 71 has an annular shape when viewed along the X-axis. The diameter of ferrule 71 is, for example, 2.5 mm.

Ferrule 71 is fitted to one end (end portion on the light receiving surface 40A side) of optical waveguide 4. In the present exemplary embodiment, the inner diameter of ferrule 71 is greater than the outer diameter of optical waveguide 4. Ferrule 71 is integrally joined to light emitting module M1 via bonding member G1.

Bonding member G1 bonds optical waveguide 4 and ferrule 71 to each other. Bonding member G1 is a cured substance of a paste-type resin adhesive agent for bonding inner circumferential surface 711 (see FIG. 5) of ferrule 71 and the outer circumferential surface of optical waveguide 4 together. The outer circumferential surface of optical waveguide 4 that is bonded to inner circumferential surface 711 is outer circumferential surface 420 of cladding 42.

Outer circumferential surface 420 of cladding 42 is in contact with inner circumferential surface 711 of ferrule 71 at contact point P3 (see FIG. 5). In other words, cladding 42 is disposed so that a portion of its outer circumferential surface 420 is in contact with inner circumferential surface 711 of ferrule 71.

Ferrule 71 is integrally joined to light emitting module M1 so that cladding 42 comes into contact with ferrule 71 at contact point P3 within ferrule 71. Cladding 42 may not necessarily be directly in contact with ferrule 71. It is possible that bonding member G1 (adhesive agent) may be interposed between cladding 42 and ferrule 71.

In the present exemplary embodiment, optical waveguide 4 is offset in the negative direction of the Z-axis within ferrule 71, when viewed from end face 710 of ferrule 71.

Core 41 is disposed off-center toward the outer circumference of cladding 42, which is opposite to contact point P3. An end portion of core 41 that is on the positive side of the Z-axis protrudes outward slightly from the outer circumferential surface 420 of cladding 42. This end portion is protruding region 43.

As illustrated in FIG. 5, first distance W1 is shorter than second distance W2 when viewed from end face 710 of ferrule 71. First distance W1 is a distance between center P1 of end face 710 and optical axis C1 of core 41. Second distance W2 is a distance between center P1 of end face 710 and center P2 of cladding 42. Optical axis C1 is an optical axis of core 41 in third region 403.

When the just-described condition is satisfied, core 41 is positioned by ferrule 71 and in particular positioned so that optical axis C1 of core 41 is located closer toward the center.

In the present exemplary embodiment, center P1 of end face 710 is located inside core 41 when viewed from end face 710. As a result, optical axis C1 of core 41 is positioned more accurately so as to be located closer toward center P1 of end face 710.

In the present exemplary embodiment, optical axis C1 of core 41 is in agreement with center P1 of end face 710 when viewed from end face 710 (see FIG. 5). In other words, first distance W1 is zero (0). As a result, optical axis C1 of core 41 is positioned at center P1 of end face 710.

Optical waveguide 4 of the present exemplary embodiment is positioned by ferrule 71 and retaining member 5 so that protruding region 43 is kept facing in the positive direction of the Z-axis from light receiving surface 40A to terminal end surface 40B.

Receptacle 81 of device body 2, which is the joining destination of ferrule 71, is described with reference to FIGS. 2 and 4. Receptacle 81 is, for example, a member integrally formed with case 20 of device body 2 and made of, for example, resin.

More specifically, receptacle 81 protrudes in the negative direction of the X-axis continuously from one end of case 20 that is on the negative side of the X-axis. Receptacle 81 may be a metal member. Receptacle 81 is a separate part from case 20 and is secured to case 20 using, as appropriate, various techniques of bonding, such as adhesive bonding, melt bonding, gluing, and coupling using fastening members (for example, screws).

Receptacle 81 as a whole has a substantially cylindrical shape. As illustrated in FIG. 2, receptacle 81 includes first portion 801 and second portion 802. First portion 801 is continuous with one end of case 20 that is on the negative side of the X-axis. Second portion 802 has a smaller outer diameter than first portion 801. Second portion 802 is continuous with one end of first portion 801 that is on the negative side of the X-axis.

Receptacle 81 includes through-hole 811 that penetrates receptacle 81 along the X-axis. Through-hole 811 is in communication with the space inside case 20 that accommodates light source 21, optical system 22, and so forth.

Fourth lens 224 of optical system 22 is disposed so as to close the opening at the inner end of through-hole 811. This means that one surface of fourth lens 224 of optical system 22 is exposed to the outside through through-hole 811 when ferrule 71 is not connected to receptacle 81.

As illustrated in FIG. 2, through-hole 811 includes smaller diameter hole 812 and larger diameter hole 813. Larger diameter hole 813 has a larger inner diameter than the inner diameter of smaller diameter hole 812. Smaller diameter hole 812 and larger diameter hole 813 are coaxial with each other and in communication with each other.

Smaller diameter hole 812 is a circular shaped hole that penetrates first portion 801. Larger diameter hole 813 is a circular shaped hole that penetrates second portion 802. The inner diameter of smaller diameter hole 812 is set to be substantially the same as the outer diameter of ferrule 71 so that ferrule 71 can be fitted into smaller diameter hole 812 with approximately no clearance therebetween.

The inner diameter of larger diameter hole 813 is set to be substantially the same as the outer diameter of holder H1 so that holder H1 can be fitted into larger diameter hole 813. The inner diameter of smaller diameter hole 812 is smaller than the outer diameter of fourth lens 224, which is disposed adjacent to smaller diameter hole 812.

The depth (i.e., dimension along the X-axis) of smaller diameter hole 812 is substantially equal to the dimension of a portion of ferrule 71 that protrudes from holder H1 in the positive direction of the X-axis. With ferrule 71 being connected to receptacle 81, holder H1 is in contact with circumferential edge portion 815 (see FIG. 2) of the opening of smaller diameter hole 812.

This prevents ferrule 71 from moving further inward. As a result, ferrule 71 does not collide with fourth lens 224 of optical system 22, preventing damage to fourth lens 224.

With holder H1 being in contact with circumferential edge portion 815 (see FIG. 2), light receiving surface 40A of optical waveguide 4 is disposed so as to be in close proximity and opposed to the surface of fourth lens 224 that is on the negative side of the X-axis. Optical axis C1 of core 41 that is positioned by ferrule 71 is in agreement with optical axis CX1 of light source 21 and optical system 22 (see FIG. 1).

The outer circumferential surface of second portion 802 is formed with above-described screw part 810 (see FIGS. 2 and 4). Screw part 810 is screw-fittable with screw thread 341 of securing cap 34.

Second portion 802 has slit-shaped groove 814 in a region of its outer circumferential surface that is on the positive side of the Y-axis. Groove 814 penetrates the just-described region of second portion 802. Groove 814 communicates with larger diameter hole 813. Groove 814 is formed extending from one end to the other end of second portion 802 along the X-axis. To groove 814, later-described protruding part H11 of holder H1 is insertable.

The width (i.e., dimension along the Z-axis) of groove 814 is substantially the same as the width of protruding part H11 so that protruding part H11 can move in the positive direction of the X-axis within groove 814. With holder H1 being in contact with circumferential edge portion 815 (see FIG. 2), protruding part H11 may move to the inner end of groove 814 in the X-axis direction.

In the present exemplary embodiment, the refractive index of bonding member G1 is lower than the refractive index of core 41. This reduces unnecessary light leakage from core 41 to bonding member G1. In third region 403 of optical waveguide 4, protruding region 43 is directly in contact with bonding member G1 and the above-described relationship of refractive index is satisfied. Therefore, light leakage can be prevented effectively.

2.3.6 Holder

At least a portion (a portion in the present exemplary embodiment) of light emitting module M1 and at least a portion (a portion in the present exemplary embodiment) of ferrule 71 are inserted into holder H1. Holder H1 is a member that joins light emitting module M1 and ferrule 71 to each other.

As illustrated in FIGS. 2 to 4, holder H1 is, for example, a cylindrical shaped member having a central axis extending along the X-axis. Holder H1 has respective openings at both end faces of the X-axis. Holder H1 is, for example, a member made of metal. Holder H1 may be made of synthetic resin. Holder H1 has a cylindrical shape having a central axis extending along the X-axis.

The inner diameter of holder H1 is larger than the outer diameter of light emitting module M1. The inner diameter of holder H1 is larger than the outer diameter of ferrule 71.

In the present exemplary embodiment, the outer diameter of ferrule 71 is substantially equal to the outer diameter of light emitting module M1, or larger than the outer diameter of light emitting module M1. When these conditions are satisfied, ferrule 71 is able to have sufficient rigidity for positioning core 41.

Holder H1 includes protruding part H11 protruding in the positive direction of the Y-axis, disposed in a region of the outer circumferential surface of holder H1 that is close to ferrule 71 along the X-axis direction. In the present exemplary embodiment, protruding part H11 is disposed on the outer circumferential surface of holder H1 that is opposite to opening 31 of cover 30, in other words, that is opposite to the contact surface in contact with skin 92.

When protruding part H11 is inserted into groove 814 in the positive direction of the X-axis, protruding part H11 positions hair cutting member 3 to determine the circumferential position of hair cutting member 3 relative to receptacle 81. That is, protruding part H11 corresponds to positioning structure Q1 (see FIG. 4). In the present exemplary embodiment, protruding part H11 has a cylindrical shape. Protruding part H11 may be in a hemispherical shape or in a prismatic shape.

A portion of light emitting module M1 (i.e., one end thereof that is on the positive side of the X-axis) is secured by securing member F1 with it being inserted inward from the opening of holder H1 that is on the negative side of the X-axis. A portion of ferrule 71 (i.e., one end thereof that is on the negative side of the X-axis) is secured by securing member F1 with one end of optical waveguide 4 (i.e., end portion on the light receiving surface 40A side) being attached to ferrule 71 and inserted inward from the opening of holder H1 that is on the positive side of the X-axis.

Specifically, hair cutting member 3 includes securing member F1 that secures light emitting module M1 and ferrule 71 inside holder H1. The refractive index of securing member F1 is lower than the refractive index of core 41.

Securing member F1 is, for example, a cured substance of a paste-type resin adhesive agent. Securing member F1 may be composed of either the same type of adhesive agent as bonding member G1 inside ferrule 71 or a different type of adhesive agent.

Securing member F1 bonds a portion of light emitting module M1 and a portion of ferrule 71 to each other. Specifically, securing member F1 bonds light emitting module M1 and ferrule 71 together so that the central axis of holder H1, the central axis of light emitting module M1, and the central axis of ferrule 71 are in agreement with each other. The central axis of ferrule 71 is in agreement with optical axis C1 of third region 403.

Optical waveguide 4 is secured by securing member F1 so that optical axis C1 of first region 401 and optical axis C3 of third region 403 are staggered from each other in holder H1. Securing member F1 brings the central axis of light emitting module M1 and the central axis of ferrule 71 into agreement with the central axis of holder H1. Securing member F1 secures optical waveguide 4 so as to be bent in second region 402.

It is desirable that the curvature of second region 402 of optical waveguide 4 be as small as possible so that the leakage of light can be reduced in second region 402.

As described above, the refractive index of securing member F1 is lower than the refractive index of core 41 in the present exemplary embodiment. This reduces unnecessary light leakage from core 41 to securing member F1. Protruding region 43 is in direct contact with securing member F1 in a portion of first region 401 and second region 402 of optical waveguide 4. When the above-described relationship of refractive index is satisfied, light leakage can be prevented effectively.

2.4. Usage Example

Next, usage examples of hair cutting device 1 according to the present exemplary embodiment will be described below with reference to FIGS. 7A to 8B.

Figure 7A:
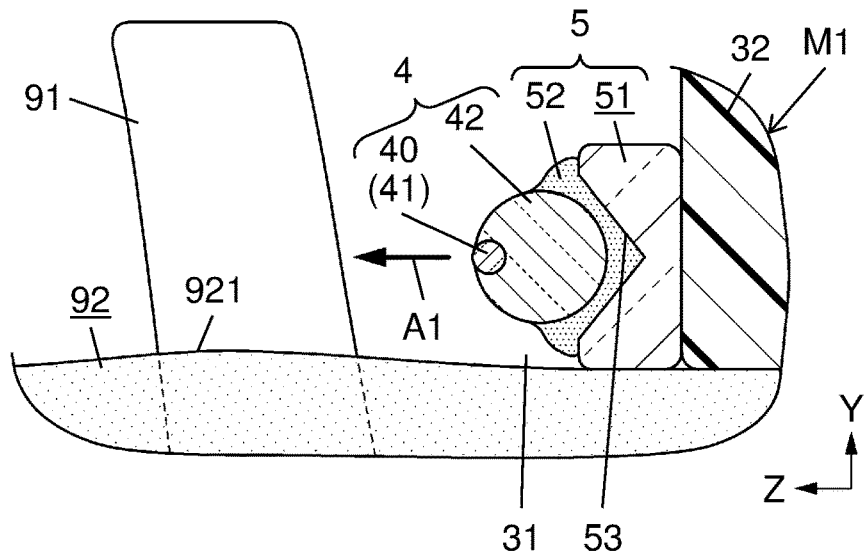
FIG. 7A is a schematic cross-sectional view illustrating the hair cutting device according to the exemplary embodiment, showing a state before the hair cutting device cuts a hair.
Figure 7B:
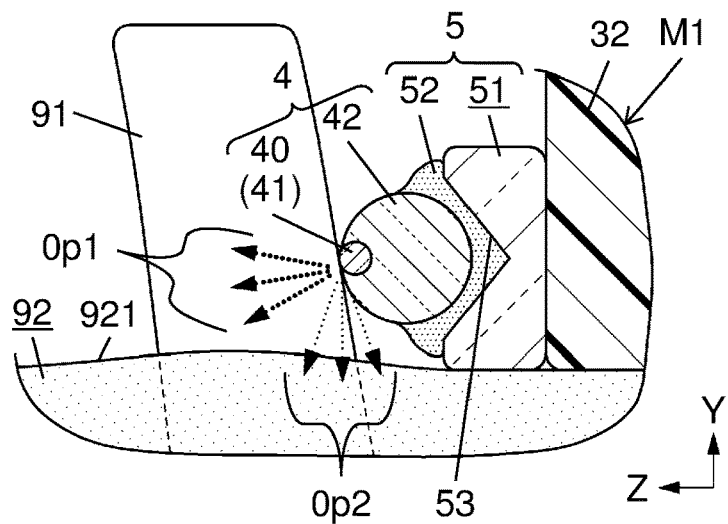
FIG. 7B is a schematic cross-sectional view illustrating the hair cutting device according to the exemplary embodiment, showing a state while the hair cutting device is cutting the hair.
Figure 7C:
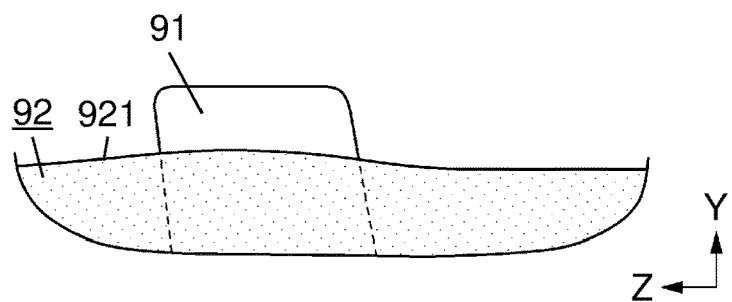
FIG. 7C is a schematic cross-sectional view illustrating the hair cutting device according to the exemplary embodiment, showing a state after the hair cutting device has cut the hair.

FIG. 7A is a schematic cross-sectional view illustrating hair cutting device 1, showing a state before hair cutting device 1 cuts hair 91. FIG. 7B is a schematic cross-sectional view illustrating hair cutting device 1, showing a state while hair cutting device 1 is cutting hair 91. FIG. 7C is a schematic cross-sectional view illustrating hair cutting device 1, showing a state after hair cutting device 1 has cut hair 91.

When using hair cutting device 1, the user grips device body 2 to bring the surface of hair cutting member 3 that is on the negative side of the Y-axis into contact with skin 92 of the user. Thus, as illustrated in FIG. 7A, hair 91, which is to be cut, is introduced from opening 31 into cover 30 so as to be opposed to light emitting portion 40 retained by retaining member 5.

As illustrated in FIG. 7A, when light emitting portion 40 is not in contact with hair 91, almost no light leakage occurs from light emitting portion 40 due to the difference in refractive index between light emitting portion 40 and the air. Under this condition, the user moves hair cutting member 3 along surface 921 of skin 92 in the direction indicated by arrow A1 (in the positive direction of Z-axis).

As illustrated in FIG. 7B, in association with movement of hair cutting member 3, light emitting portion 40 comes into contact with hair 91 located in the moving direction of hair cutting member 3 (i.e., in the positive direction of the Z-axis). Because the refractive index of light emitting portion 40 is lower than the refractive index of hair 91, light leaks out of light emitting portion 40 when light emitting portion 40 comes into contact with hair 91. As a result, light emitting portion 40 causes hair 91 to be irradiated with light.

As illustrated in FIG. 7B, part of the light emitted from light emitting portion 40 is also applied to skin 92 around hair 91. Herein, the light applied to hair 91 is referred to as first emission light Op1 and the light applied to skin 92 is referred to as second emission light Op2. First emission light Op1 is emitted from protruding region 43, and second emission light Op2 is emitted from cladding 42.

By the energy of first emission light Op1 emitted by light emitting portion 40, hair 91 is cut. In the present exemplary embodiment, the wavelength of the light generated by light source 21 and passing through optical waveguide 4 (for example, from 400 nm to 700 nm) includes a wavelength of light that is absorbed by a chromophore in hair 91. A chromophore is an atomic group that is necessary for a compound, particularly an organic compound, to exhibit a color.

Accordingly, first emission light Op1 is absorbed by a chromophore in hair 91 and is thereby converted into heat. The resulting heat destroys the molecular bonds of hair 91, or causes hair 91 to be melted or burnt. The chromophore, which can be a target of first emission light Op1, is contained in keratin or water, for example.

As described previously, when the user moves hair cutting member 3, serving as hair cutting device 1, along skin 92 in the direction indicated by arrow A1 (see FIG. 7A), the user is able to cut hair 91. As illustrated in FIG. 7C, after optical waveguide 4 has passed, only the root portion of hair 91 that has not been cut remains on skin 92.

However, as illustrated in FIG. 7B, even when light emitting portion 40 does not come into contact with hair 91, it is also possible that hair 91 may be irradiated with light due to leakage of evanescent waves from the interface between light emitting portion 40 and the air toward the air. This means that hair 91 may be cut not only when light emitting portion 40 comes into contact with hair 91 but also when light emitting portion 40 comes close to just before being in contact with hair 91.

Figure 8A:
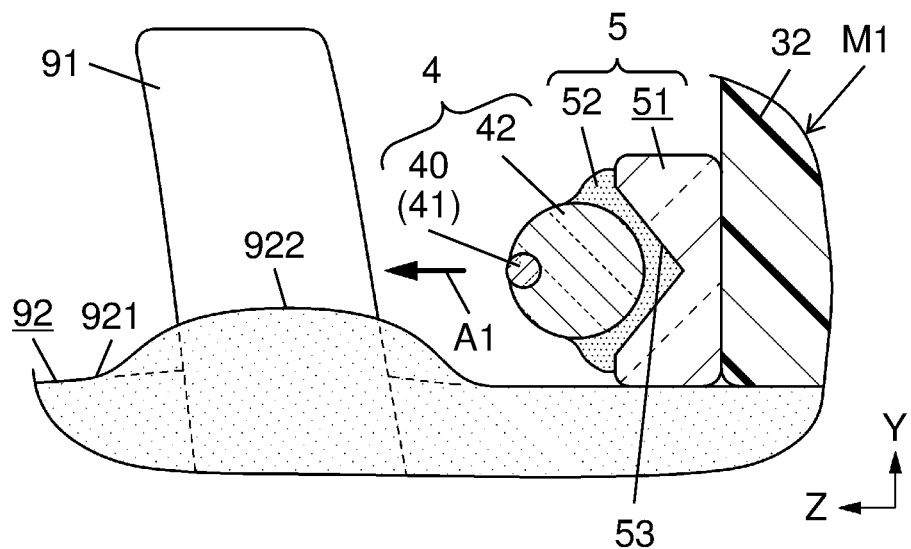
FIG. 8A is a schematic cross-sectional view illustrating the hair cutting device according to the exemplary embodiment, showing another state before the hair cutting device cuts a hair.
Figure 8B:
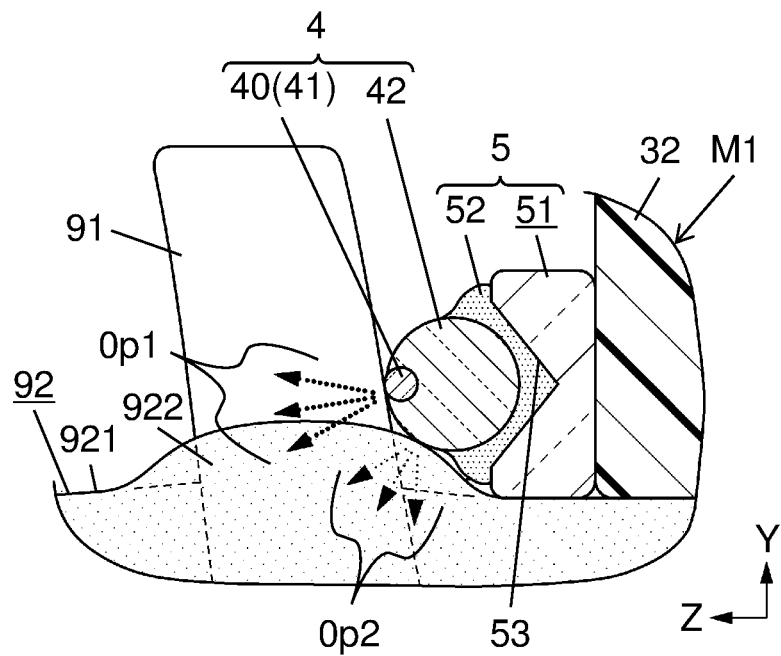
FIG. 8B is a schematic cross-sectional view illustrating the hair cutting device according to the exemplary embodiment, showing another state while the hair cutting device is cutting the hair.

Depending on the condition of skin 92, light emitting portion 40 may come into contact with a portion of skin 92 when cutting hair 91 with the user of hair cutting device 1. FIGS. 8A and 8B are schematic cross-sectional views respectively showing hair cutting device 1 before cutting hair and while cutting hair in cases where raised portion 922 is present on skin 92 around hair 91. Raised portion 922 may be, for example, a pimple.

As illustrated in FIG. 8A, when light emitting portion 40 is not in contact with hair 91, almost no light leakage occurs from light emitting portion 40 due to the difference in refractive index between light emitting portion 40 and the air. Under this condition, the user moves hair cutting member 3 along surface 921 of skin 92 in the direction indicated by arrow A1.

As illustrated in FIG. 7B, in association with movement of hair cutting member 3, light emitting portion 40 comes into contact with hair 91 located on the positive side of the Z-axis. At that time, hair 91 is irradiated with first emission light Op1 leaking out of light emitting portion 40 due to the difference in refractive index between light emitting portion 40 and hair 91. Hair 91 is cut by the energy of first emission light Op1.

As illustrated in FIG. 8B, light emitting portion 40 may also come into contact with raised portion 922 around skin. Because the refractive index of light emitting portion 40 is lower than the refractive index of surface 921 of skin 92, light leaks out of light emitting portion 40 when light emitting portion 40 comes into contact with skin 92. As a result, light emitting portion 40 causes skin 92 to be irradiated with second emission light Op2.

However, because second emission light Op2 is emitted from cladding 42, the energy of second emission light Op2 is lower than the energy of first emission light Op1 emitted from protruding region 43.

2.5 Replacement of Hair Cutting Member

In the present exemplary embodiment, ferrule 71 is detachably mounted to receptacle 81. Therefore, hair cutting member 3 can be replaced easily. Hereinbelow, replacement work of hair cutting member 3 will be described.

When light emitting portion 40 of optical waveguide 4 makes contact with skin 92 and hair 91 repeatedly, damages are caused on light emitting portion 40, and the amount of the light emitted from hair cutting member 3 is accordingly reduced. When this is the case, the user carries out replacement work of hair cutting member 3.

Specifically, when the user rotates securing cap 34 in a loosening direction, securing cap 34 moves in the negative direction of the X-axis and finally comes off from receptacle 81.

In this condition, by gripping cover 30 and pulling it in the negative direction of the X-axis, the user is able to pull out ferrule 71 and light emitting module M1 in the negative direction of the X-axis. At that time, protruding part H11 (positioning structure Q1) fitted in groove 814 also moves along groove 814 in the negative direction of the X-axis, and finally comes off from groove 814 (see FIG. 2).

Subsequently, the user attaches new hair cutting member 3 to device body 2. Specifically, the user grips cover 30 and presses ferrule 71 in the positive direction of the X-axis to insert ferrule 71 into receptacle 81.

At that time, the user adjusts the circumferential angle of hair cutting member 3 so that protruding part H11 is opposed to groove 814 in the X-axis direction while using protruding part H11 (positioning structure Q1) of holder H1 as a guide mark. The user presses cover 30 in the positive direction of the X-axis and inserts protruding part H11 into groove 814.

Thereby, ferrule 71 is fitted into smaller diameter hole 812 inside receptacle 81, and holder H1 is fitted into larger diameter hole 813 of receptacle 81. Positioning structure Q1 is inserted into groove 814 to restrict rotation of hair cutting member 3 in circumferential directions relative to device body 2. As a result, light receiving surface 40A is opposed in close proximity to optical system 22 (fourth lens 224), and optical axis C1 of core 41 automatically comes into agreement with optical axis CX1 of optical system 22.

Ferrule 71 is integrally joined to light emitting module M1 so as to position core 41. When attaching hair cutting member 3 to device body 2, the user only needs to pay attention to ferrule 71 to connect ferrule 71 to receptacle 81. As a result, light emitting module M1 is positioned easily, and ease of assembly is improved for hair cutting member 3, device body 2, and hair cutting device 1.

At the time of replacement, the user does not need to bring optical axis C1 of core 41 into agreement with optical axis CX1 of device body 2 while checking the position of optical waveguide 4, in particular, the position of optical axis C1 of core 41. This means that the optical system is easily adjustable.

Finally, when the user attaches securing cap 34 to receptacle 81, hair cutting member 3 does not easily come off from device body 2.

Thus, hair cutting member 3 is detachably mounted to receptacle 81 of device body 2. As a result, ease of assembly is improved, and the optical system can be adjusted easily.

The foregoing example has illustrated replacement work by the user. However, improvement in ease of assembly relates to assembly work by workers during manufacture, not just to the replacement work by the user.

It is not essential that ferrule 71 is detachable from receptacle 81. Ferrule 71 may not be able to be detached from receptacle 81 by the user. In that case as well, light emitting module M1 is easily positioned merely by connecting ferrule 71 to receptacle 81 while only paying attention to ferrule 71 during manufacture. As a result, ease of assembly is improved for hair cutting member 3, device body 2, and hair cutting device 1.

The worker does not need to bring optical axis C1 of core 41 into agreement with optical axis CX1 of device body 2 while paying attention to the position of optical axis C1 of core 41. As a result, the optical system is easily adjustable.

2.6 Control Circuit

Figure 9:
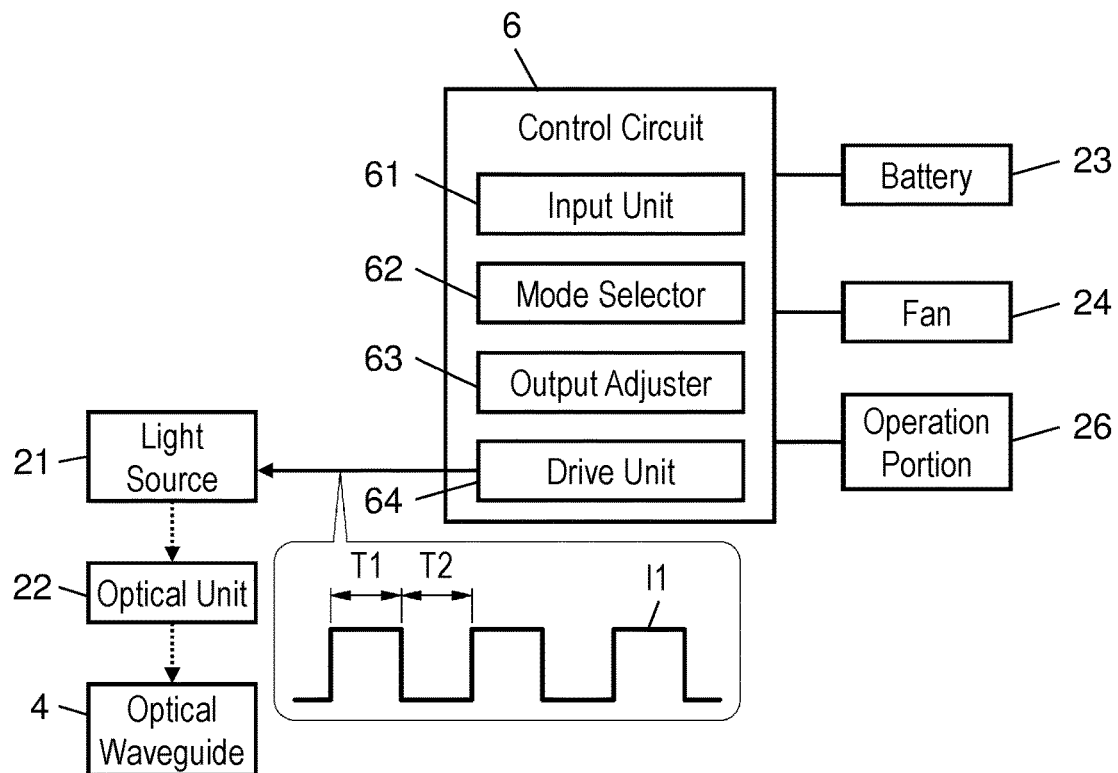
FIG. 9 is a block diagram schematically illustrating the configuration of a control circuit of the hair cutting device according to the exemplary embodiment.

Next, the configuration of control circuit 6 will be described with reference to FIG. 9. FIG. 9 is a block diagram schematically illustrating the configuration of control circuit 6 of hair cutting device 1.

As illustrated in FIG. 9, control circuit 6 is electrically connected to light source 21, battery 23, fan 24, and operation portion 26. Control circuit 6 includes input unit 61, mode selector 62, output adjuster 63, and drive unit 64.

Control circuit 6 includes, for example, a microcomputer including a processor and a memory. The processor reads out a program recorded in the memory and executes the processes described in the program, to function as control circuit 6.

In the present exemplary embodiment, the program is pre-recorded in the memory during manufacture. The program may be provided after manufacture via a non-volatile memory storage medium, such as a memory card, or via an electronic telecommunication network.

Operation portion 26 outputs, to input unit 61, the information according to user operations, such as turning on/off of light source 21.

Mode selector 62 switches the operating mode of light source 21 to either a first mode or a second mode according to the information sent from input unit 61. The operating modes of light source 21 will be described later.

Drive unit 64 supplies drive current I1 to light source 21, which is composed of a semiconductor laser, to operate light source 21. As illustrated in FIG. 9, drive unit 64 supplies pulsed drive current I1 for alternately repeating light emission period T1 and light-off period T2 to light source 21. In response to this drive current I1, light source 21 intermittently generates light.

Specifically, light source 21 emits light in light emission period T1 of drive current I1 and turns off in light-off period T2 of drive current H. Therefore, light source 21 blinks according to the frequency of drive current H. In the present exemplary embodiment, the duty rate of drive current I1 is 50%. The duty rate means the proportion of light emission period T1 per one cycle of drive current H. Thus, light emission period T1 is equal to light-off period T2.

In the first mode, mode selector 62 sets light emission period T1 to be less than or equal to $1/10,000$th of a second. The first mode is a mode in which protection to skin 92 is prioritized. In other words, in the first mode, drive unit 64 operates light source 21 with drive current I1 having a frequency of higher than or equal to 5 kHz. In the present exemplary embodiment, light emission period T1 in the first mode is $1/15,000$th of a second.

In the second mode, mode selector 62 sets light emission period T1 to be greater than or equal to $1/100$th of a second. The second mode is a mode in which cutting of hair 91 is prioritized. In other words, in the second mode, drive unit 64 operates light source 21 with drive current I1 having a frequency of less than or equal to 50 kHz. In the present exemplary embodiment, light emission period T1 in the second mode is $1/80$ of a second.

Output adjuster 63 controls drive unit 64 according to the information sent from input unit 61 to adjust the output of light source 21. The output of light source 21 includes the intensity (brightness) and wavelength of the light generated by light source 21.

Output adjuster 63 adjusts the output of light source 21 to adjust the power density of the light passing through optical waveguide 4. Specifically, output adjuster 63 changes the magnitude of drive current I1 supplied from drive unit 64 to thereby adjust the power density of the light.

Figure 10:
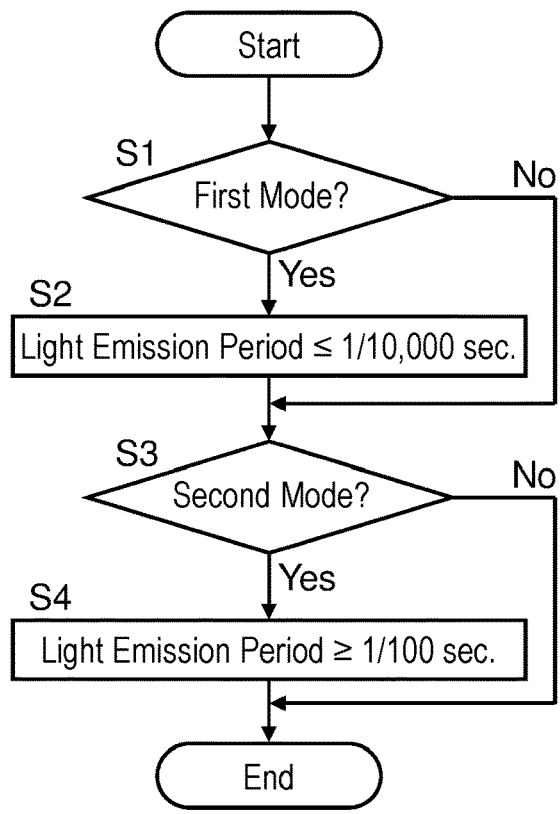
FIG. 10 is a flowchart illustrating operations of the hair cutting device according to the exemplary embodiment.

Next, the operations of hair cutting device 1 provided with the just-described control circuit 6 will be described with reference to FIG. 10. FIG. 10 is a flowchart illustrating operations of hair cutting device 1.

In step S1, control circuit 6 determines whether or not the operating mode of light source 21 is the first mode. If the operating mode is the first mode, control circuit 6 sets light emission period T1 to less than or equal to $1/10,000$th of a second in step S2. If the operating mode is not the first mode, control circuit 6 moves the process to step S3.

In step S3, control circuit 6 determines whether or not the operating mode of light source 21 is the second mode. If the operating mode is the second mode, control circuit 6 sets light emission period T1 to greater than or equal to $1/100$ of a second in step S4. If the operating mode is not the second mode, control circuit 6 ends the process.

Hair cutting device 1 repeatedly performs the above-described steps S1 to S4. The flowchart shown in FIG. 10 is an example of the operations of hair cutting device 1. For example, the sequence of the steps may be altered. Furthermore, any of the steps may be eliminated, or other steps may be added as appropriate.

In the state where hair cutting member 3 is detached from device body 2, fourth lens 224 of optical system 22 that is disposed at the inner end of through-hole 811 of receptacle 81 is exposed through through-hole 811.

Device body 2 further includes a detector (not shown) that senses whether or not hair cutting member 3 is attached thereto. The detector may include, for example, a switch (for example, pressure sensor) disposed on receptacle 81 so as to receive a pressing force from a protrusion disposed on hair cutting member 3 (holder H1).

When hair cutting member 3 is attached to device body 2, the switch receives a pressing force from the protrusion and is turned on. When hair cutting member 3 is detached from device body 2, the switch is turned off. The detector is electrically connected to control circuit 6. When control circuit 6 recognizes detachment of hair cutting member 3 based on an output signal from the detector, control circuit 6 stops light source 21.

For example, even when the user performs an operation of actuating light source 21 with hair cutting member 3 being not attached, it is possible to prevent light emission from receptacle 81. When hair cutting member 3 is detached from device body 2 with light source 21 having been turned on, control circuit 6 stops light source 21 based on an output signal from the detector. This prevents light emission from receptacle 81.

3. Operation

Next, operations and advantageous effects of hair cutting device 1 according to the present exemplary embodiment will be described below.

Cutting of hair 91, which is the basic function of hair cutting device 1, is performed according to the principle discussed in section "2.4. Usage Example".

In the present exemplary embodiment, first emission light Op1 of light emitting portion 40 has a wavelength of from 400 nm to 700 nm. Therefore, first emission light Op1 is easily absorbed by a chromophore contained hair 91, such as keratin or water, for example.

The power density of the light passing through optical waveguide 4 is higher than or equal to 50 kW/cm$^2$ at least at the time of cutting hair 91. Therefore, first emission light Op1 applied from light emitting portion 40 to hair 91 has a sufficient power density for cutting hair 91 (higher than or equal to 50 kW/cm$^2$).

Next, an effect on skin 92, which is a secondary function of hair cutting device 1, will be described. As described previously, second emission light Op2 applied to skin 92, as well as first emission light Op1, has a wavelength of from 400 nm to 700 nm.

When second emission light Op2 has a wavelength of 400 nm to 450 nm, for example, second emission light Op2 is expected to have a bactericidal effect against the bacteria existing on skin 92, such as Cutibacterium *acnes*. As illustrated in FIGS. 8A and 8B, when raised portion 922 such as a pimple is present around hair 91, second emission light Op2 is directly applied to raised portion 922, so a more effective bactericidal effect can be expected.

When second emission light Op2 has a wavelength of, for example, 450 nm to 700 nm, skin 92 is activated by irradiation with second emission light Op2. As a result, an advantageous effect called "beautiful skin effect" can be expected, such as an improvement in quality of skin.

The present exemplary embodiment is expected to have an advantageous effect of improvement in ease of assembly, as described in section "2.5 Replacement of Hair Cutting Member".

In the present exemplary embodiment, ferrule 71 is integrally joined to light emitting module M1 in such a manner as to retain an end portion of optical waveguide 4. Ferrule 71 positions core 41 with respect to light that is introduced into optical waveguide 4.

Therefore, when attaching hair cutting member 3 to device body 2, the user only needs to pay attention to ferrule 71 to connect ferrule 71 to receptacle 81. As a result, light emitting module M1 is positioned easily, and ease of assembly is improved for hair cutting device 1.

In the present exemplary embodiment, optical waveguide 4 (optical fiber) is not provided in device body 2, but is provided only in hair cutting member 3. This serves to further improve ease of assembly of hair cutting device 1.

Holder H1 joins light emitting module M1 and ferrule 71 together. This enables light emitting module M1 and ferrule 71 to be easily connected to receptacle 81. As a result, ease of assembly of hair cutting device 1 is further improved.

Optical axis C1 of core 41 (third region 403) is non-coaxial with optical axis C2 of light emitting module M1 (first region 401). This increases the freedom in the positional relationship between ferrule 71 and light emitting module M1 and also improves ease of assembly of hair cutting device 1. It is also possible to simplify the structure (cylindrical shape) of holder H1.

Core 41 is disposed off-center toward the outer circumference of cladding 42. As a result, for example, core 41 can be easily disposed closer toward the center within ferrule 71.

The present exemplary embodiment is expected to exhibit an advantageous effect of being able to adjust the optical system easily, as described in section "2.5 Replacement of Hair Cutting Member".

In the present exemplary embodiment, first distance W1 is shorter than second distance W2 when viewed from end face 710 of ferrule 71. This allows optical axis C1 of core 41 to be disposed closer toward the center of ferrule 71 easily.

As a result, the optical system is easily adjustable when, for example, replacing and assembling hair cutting member 3. Because ferrule 71 positions core 41, it is unnecessary to bring optical axis C1 of core 41 into agreement with optical axis CX1 of device body 2 while checking the position of optical axis C1.

In the present exemplary embodiment, center P1 of end face 710 is located inside core 41. Thus, the reliability related to the adjustment of the optical system is further improved.

Optical axis C1 of core 41 is in agreement with center P1 of end face 710 when viewed from end face 710. This means that the central axis of ferrule 71 should be brought into agreement with optical axis CX1 of optical system 22 with ferrule 71 being inserted in smaller diameter hole 812 of receptacle 81.

In replacing and assembling hair cutting member 3, optical axis C1 of core 41 comes into agreement with optical axis CX1 by merely connecting ferrule 71 to receptacle 81. As a result, the reliability related to the adjustment of the optical system is further improved.

Cladding 42 is disposed so that a portion of its outer circumferential surface 420 comes into contact with inner circumferential surface 711 of ferrule 71. In other words, when outer circumferential surface 420 of cladding 42 is disposed so as to come into contact with inner circumferential surface 711 of ferrule 71 at contact point P3 in the manufacture of hair cutting member 3, the off-centered core 41 is automatically disposed closer toward the center of ferrule 71.

When bonding optical waveguide 4 to ferrule 71 with bonding member G1, it is difficult to bring core 41 of core 41 into agreement with center P1 of end face 710 of ferrule 71 at the stage before bonding member G1 cures.

However, when outer circumferential surface 420 of cladding 42 is brought into contact with inner circumferential surface 711 of ferrule 71, bonding member G1 cures in such a state that core 41 is in agreement with center P1 of end face 710 stably. As a result, the optical system is further more easily adjustable.

In the present exemplary embodiment, core 41 is disposed in an outer circumferential portion of cladding 42, and a portion of core 41 (i.e., protruding region 43) is exposed from the outer circumferential portion. Accordingly, for example, in a portion of optical waveguide 4 that is exposed from opening 31 of cover 30 and opposed to hair 91, it is unnecessary to remove at least a portion of cladding 42 to expose at least a portion of core 41.

4. Modified Examples

The present exemplary embodiment is merely one embodiment of the present disclosure. The present exemplary embodiment can be modified as appropriate as long as the objects of the present disclosure are achieved.

In the following, modified examples of the present exemplary embodiment are listed. These modified examples may be combined as appropriate. Hair cutting device 1 described hereinabove is referred to as a "basic embodiment". In the following modified examples, the constituent elements that are substantially identical to those of the basic embodiment are designated by the same reference signs, and repetitive description thereof is omitted as appropriate.

4.1 First Modified Example

Hair cutting devices 1A to 1D according to a first modified example of the present exemplary embodiment are described with reference to FIGS. 11A to 11D. FIGS. 11A to 11D each schematically illustrate an external appearance of the first modified example of hair cutting device 1.

As illustrated in FIG. 11A, hair cutting device 1A as a whole has a substantially Y shaped external appearance. Device body 2 of hair cutting device 1A further includes coupling part J1 that connects receptacle 81 to case 20. In these respects, hair cutting device 1A is different from the basic embodiment.

Hair cutting member 3 of hair cutting device 1A has the same dimensions and shape as hair cutting member 3 of the basic embodiment. The dimensions and shape of hair cutting member 3 of hair cutting device 1A may be different from those of hair cutting member 3 of the basic embodiment. Hair cutting member 3 of hair cutting device 1A has an elongated cylindrical shape having a central axis extending along the X-axis. Case 20 of hair cutting device 1A has an elongated prismatic shape having a central axis extending along the Z-axis.

Coupling part J1 has a bent cylindrical shape. Coupling part J1 protrudes in the positive direction of the Z-axis from one end of case 20 that is on the positive side of the Z-axis. Coupling part J1 is bent in such a manner that it is more distant from the Z-axis as it is toward the positive direction of the Z-axis. Coupling part J1 is bent in the positive direction of the Z-axis, and thereafter bent in the negative direction of the X-axis so as to be connected to receptacle 81. In the first modified example, coupling part J1 is integrally formed with receptacle 81.

Coupling part J1 accommodates three mirror devices K1. Respective mirror devices K1 are disposed at corresponding bent portions inside coupling part J1, and each of mirror devices K1 reflects the light emitted from optical system 22 within case 20 in a predetermined direction. This allows coupling part J1 to guide the light emitted from optical system 22 to light receiving surface 40A within ferrule 71 inserted in receptacle 81 (cf. optical axis CX1).

In hair cutting device 1A, hair cutting member 3 is detachable from receptacle 81 of device body 2 along the X-axis. Hair cutting device 1A has a crossing shape in which the longitudinal axis of hair cutting member 3 intersects (more specifically, orthogonally intersects) the longitudinal axis of case 20. The term "crossing shape" means such a shape that the longitudinal axis of hair cutting member 3 intersects the longitudinal axis of case 20 when ferrule 71 is connected to receptacle 81.

Case 20 includes receptacle 83 that is detachably connected to an end portion of coupling part J1 that is opposite to receptacle 81. If hair cutting member 3 is connected to receptacle 83 without coupling part J1, the external appearance of hair cutting device 1A will be the same as that of the basic embodiment.

As illustrated in FIG. 11B, hair cutting device 1B as a whole has a substantially T shaped external appearance. Device body 2 of hair cutting device 1B further includes coupling part J2 that connects receptacle 81 and case 20 together. In these respects, hair cutting device 1B is different from the basic embodiment. Except for coupling part J2, hair cutting device 1B is substantially the same as hair cutting device 1A.

Coupling part J2 has a bent cylindrical shape. Coupling part J2 protrudes in the positive direction of the Z-axis from one end of case 20 that is on the positive side of the Z-axis. Coupling part J2 is bent in the positive direction of the X-axis. Coupling part J2 is further bent in the positive direction of the Z-axis, and thereafter bent in the negative direction of the X-axis so as to be connected to receptacle 81. In the first modified example, coupling part J2 is integrally formed with receptacle 81.

Coupling part J2 accommodates three mirror devices K1. Respective mirror devices K1 are disposed at corresponding bent portions inside coupling part J2, and each of mirror devices K1 reflects the light emitted from optical system 22 within case 20 in a predetermined direction. This allows coupling part J2 to guide the light emitted from optical system 22 to light receiving surface 40A within ferrule 71 inserted in receptacle 81 (cf. optical axis CX1).

In hair cutting device 1B, hair cutting member 3 is detachable from receptacle 81 of device body 2 along the X-axis. Hair cutting device 1B has a crossing shape in which the longitudinal axis of hair cutting member 3 intersects (more specifically, orthogonally intersects) the longitudinal axis of case 20.

As with hair cutting device 1A, case 20 includes receptacle 83 that is detachably connected to an end portion of coupling part J2 that is opposite to receptacle 81. If hair cutting member 3 is connected to receptacle 83 without coupling part J2, the external appearance of hair cutting device 1B will be the same as that of the basic embodiment.

As illustrated in FIG. 11C, hair cutting device 1C as a whole has a substantially L shaped external appearance. Device body 2 of hair cutting device 1C further includes coupling part J3 that connects receptacle 81 and case 20 together. In these respects, hair cutting device 1C is different from the basic embodiment. Except for coupling part J3, hair cutting device 1C is substantially the same as hair cutting device 1A.

Coupling part J3 has a cylindrical shape having a central axis extending along the Z-axis. Coupling part J3 protrudes in the positive direction of the Z-axis from one end of case 20 that is on the positive side of the Z-axis. Coupling part J3 is bent in the negative direction of the X-axis so as to be connected to receptacle 81. In the first modified example, coupling part J3 is integrally formed with receptacle 81.

Coupling part J3 accommodates mirror device K1. Mirror device K1 is disposed at a bent portion inside coupling part J3, and mirror device K1 reflects the light emitted from optical system 22 within case 20 in the negative direction of the X-axis. This allows coupling part J3 to guide light to light receiving surface 40A within ferrule 71 inserted in receptacle 81 (cf. optical axis CX1).

In hair cutting device 1C, hair cutting member 3 is detachable from receptacle 81 of device body 2 along the X-axis. Hair cutting device 1C has a crossing shape in which the longitudinal axis of hair cutting member 3 intersects (more specifically, orthogonally intersects) the longitudinal axis of case 20.

As with hair cutting device 1A, case 20 includes receptacle 83 that is detachably connected to an end portion of coupling part J3 that is opposite to receptacle 81. If hair cutting member 3 is connected to receptacle 83 without coupling part J3, the external appearance of hair cutting device 1C will be the same as that of the basic embodiment.

As illustrated in FIG. 11D, hair cutting device 1D as a whole has a substantially card shaped external appearance. Device body 2 of hair cutting device 1D further includes coupling part J4 that connects receptacle 81 and case 20 to each other, and case 20 has a different shape from that of the basic embodiment. In these respects, hair cutting device 1D is different from the basic embodiment.

Case 20 of hair cutting device 1D has a flat rectangular shape that is parallel to the X-Z plane. Coupling part J4 has a substantially L shaped cylindrical shape that is elongated along the X-axis. Coupling part J4 includes an opening in its end face that is on the negative side of the Z-axis. The interior of coupling part J4 communicates with the interior of case 20 through the opening of case 20 that is on the positive side of the Z-axis. Coupling part J4 includes protruding portion J40 protruding in the positive direction of the Z-axis, which is disposed at its edge portion on the positive side of the X-axis in the end face that is on the positive side of the Z-axis.

Receptacle 81 is disposed on an end face of protruding portion J40 that is on the negative side of the X-axis. In the first modified example, protruding portion J40 is integrally formed with receptacle 81. In the first modified example, cover 30 of hair cutting member 3 includes an opening in its end face facing the positive side of the Z-axis.

Coupling part J4 includes mirror device K1 inside protruding portion J40. Mirror device K1 reflects the light emitted from optical system 22 in the negative direction of the X-axis to guide the light to light receiving surface 40A within ferrule 71 inserted in receptacle 81 (cf. optical axis CX1).

In hair cutting device 1D, hair cutting member 3 is detachable from receptacle 81 of device body 2 along the X-axis. Owing to its shape, hair cutting device 1D can be placed in, for example. a pocket of clothing to be carried about. Hair cutting device 1D has a crossing shape in which the longitudinal axis of hair cutting member 3 intersects (more specifically, orthogonally intersects) the longitudinal axis of case 20.

4.2 Second Modified Example

Figure 12A:
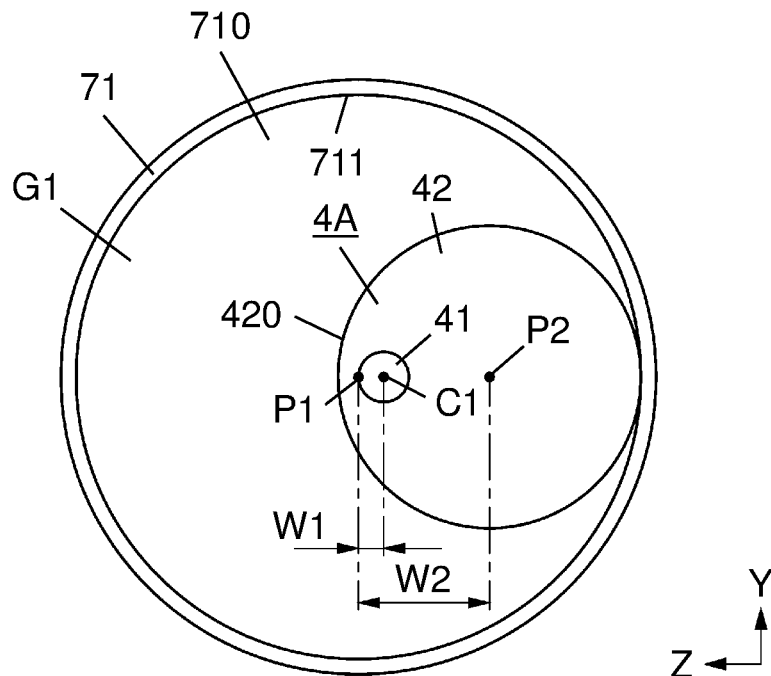
FIG. 12A is a plan view of a hair cutting device according to a second modified example of the exemplary embodiment, viewed from an end face of the ferrule.

Hair cutting device 1 according to a second modified example of the present exemplary embodiment is described with reference to FIGS. 12A and 12B. FIG. 12A is a plan view of hair cutting device 1 of the second modified example, viewed from an end face of the ferrule.

As illustrated in FIG. 12A, in optical waveguide 4A of hair cutting device 1 of the second modified example, optical axis C1 of third region 403 of core 41 is not in agreement with center P1 of end face 710 of ferrule 71. In this respect, the second modified example is different from the basic embodiment. In the second modified example, center P1 of end face 710 is positioned at the outer circumferential edge of core 41.

In optical waveguide 4A, first distance W1 is shorter than second distance W2 when viewed from end face 710 of ferrule 71. This allows ferrule 71 to position core 41 so that optical axis C1 of core 41 is brought closer toward center P1 of end face 710.

Core 41 of optical waveguide 4A is not exposed from cladding 42 at least in third region 403 (see FIG. 2). Therefore, the light leakage from optical waveguide 4A within ferrule 71 is further reduced in comparison with the basic embodiment.

In the second modified example, in at least a portion of optical waveguide 4A that is exposed from opening 31 of cover 30, at least a portion of cladding 42 is removed to expose at least a portion of core 41.

Figure 12B:
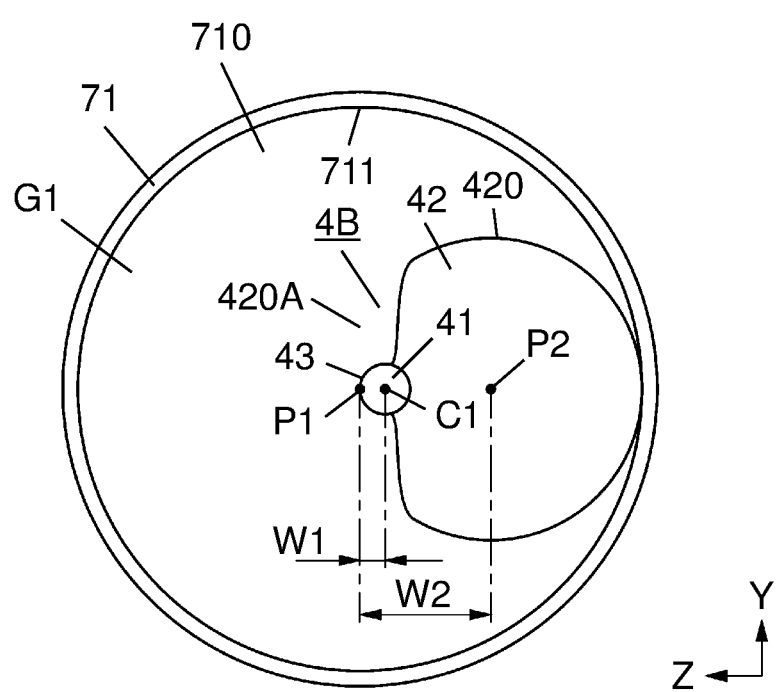
FIG. 12B is a plan view of a hair cutting device of another example according to the second modified example of the exemplary embodiment, viewed from an end face of the ferrule.

FIG. 12B is a plan view of another example of hair cutting device 1 of the second modified example, viewed from an end face of the ferrule. As illustrated in FIG. 12B, in optical waveguide 4B as well as optical waveguide 4, optical axis C1 is not in agreement with center P1 of end face 710 of ferrule 71. Here, center P1 of end face 710 is positioned at the outer circumferential edge of core 41.

In optical waveguide 4B, first distance W1 is shorter than second distance W2 when viewed from end face 710 of ferrule 71. This allows ferrule 71 to position core 41 so that optical axis C1 of core 41 is brought closer toward center P1 of end face 710.

In optical waveguide 4B, unlike optical waveguide 4A, outer circumferential surface 420 of cladding 42 has a substantially D shape such that a portion of cladding 42 is removed when viewed from end face 710 of ferrule 71.

In other words, outer circumferential surface 420 of cladding 42 includes curved surface 420A that is substantially parallel to the X-Y plane and slightly curved. Outer circumferential surface 420 of cladding 42 includes curved surface 420A extending from light receiving surface 40A to terminal end surface 40B.

Herein, approximately more than a half portion of core 41 is exposed outward from curved surface 420A when viewed from end face 710 of ferrule 71. Core 41 of optical waveguide 4B includes protruding region 43 protruding in the positive direction of the Z-axis from curved surface 420A of cladding 42. Core 41 includes protruding region 43 extending from light receiving surface 40A to terminal end surface 40B.

Therefore, unlike optical waveguide 4A, optical waveguide 4B does not need to remove at least a portion of cladding 42 in a portion that is exposed from opening 31 of cover 30.

As another example of optical waveguide 4B, the outer circumferential surface of core 41 may also have a substantially D shape such that a portion of core 41 is removed, like cladding 42, when viewed from end face 710 of ferrule 71. In this case, a surface of core 41 that is parallel to the X-Y plane may be flush with curved surface 420A of cladding 42 and may be exposed from cladding 42. Curved surface 420A may be a flat surface that is parallel to the X-Y plane.

4.3 Third Modified Example

Figure 13A:
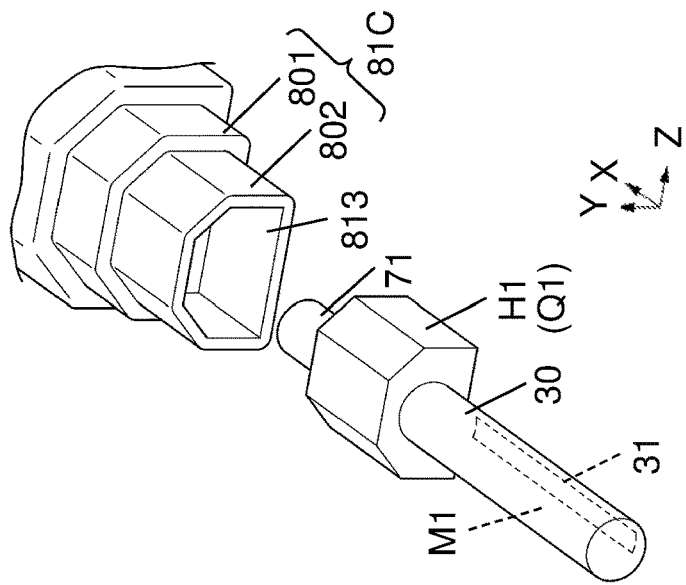
FIG. 13A is a perspective view illustrating a major part of a hair cutting device according to a third modified example of the exemplary embodiment.

Hair cutting device 1 according to a third modified example of the present exemplary embodiment is described with reference to FIGS. 13A to 15C. FIG. 13A is a perspective view illustrating a major part of hair cutting device 1 of the third modified example.

As illustrated in FIG. 13A, receptacle 81A includes groove 814A into which protruding part H11 (positioning structure Q1) of holder H1 can be inserted. The structure of groove 814A is different from groove 814 of receptacle 81 of the basic embodiment.

Specifically, second portion 802 of receptacle 81A has slit-shaped groove 814A in a region of its outer circumferential surface that is on the positive side of the Y-axis. Groove 814A penetrates the just-mentioned region of second portion 802. As a result, groove 814A allows the outside of the outer circumferential surface of second portion 802 to communicate with larger diameter hole 813.

Groove 814A includes first groove 816 and second groove 817. First groove 816 extends along the X-axis from one end of second portion 802 that is on the negative side of the X-axis to the other end thereof that is on the positive side of the X-axis. Second groove 817 extends along the circumferential direction (clockwise in FIG. 13A) from one end thereof to the other end. The one end of second groove 817 is the one end of first groove 816.

The width of first groove 816 is substantially equal to the width of second groove 817. At the above-mentioned other end of second groove 817, substantially circular shaped engaging hole 818 is disposed. The inner diameter of engaging hole 818 is slightly greater than the width of first groove 816 and second groove 817 and is substantially equal to the outer diameter of protruding part H11.

To attach hair cutting member 3 to device body 2, protruding part H11 is pressed into first groove 816 and inserted in the positive direction of the X-axis while causing second portion 802 to elastically deform in a radial direction. When protruding part H11 reaches the inner end of first groove 816, hair cutting member 3 is turned clockwise in FIG. 13A.

Protruding part H11 moves clockwise in FIG. 13A along second groove 817 while causing second portion 802 to elastically deform in a radial direction. When protruding part H11 reaches engaging hole 818 and protruding part H11 engages with engaging hole 818, second portion 802 returns to the original shape.

With hair cutting device 1 of the third modified example, hair cutting member 3 is turned in a circumferential direction in order to attach hair cutting member 3 to device body 2. For this reason, the position of protruding part H11 on the circumferential surface of holder H1 needs to be offset in advance in a circumferential direction so that opening 31 of cover 30 faces in the negative direction of the Y-axis when protruding part H11 engages with engaging hole 818.

With the configuration of the third modified example, because protruding part H11 (positioning structure Q1) is fitted in groove 814A, it is easy to carry out the circumferential positioning of hair cutting member 3 relative to receptacle 81A. As a result, ease of assembly of hair cutting device 1 is improved.

In FIG. 13A, securing cap 34 and screw part 810 screw-fitted to screw thread 341 (restraining structure U1) of securing cap 34 are not shown.

Figure 14A:
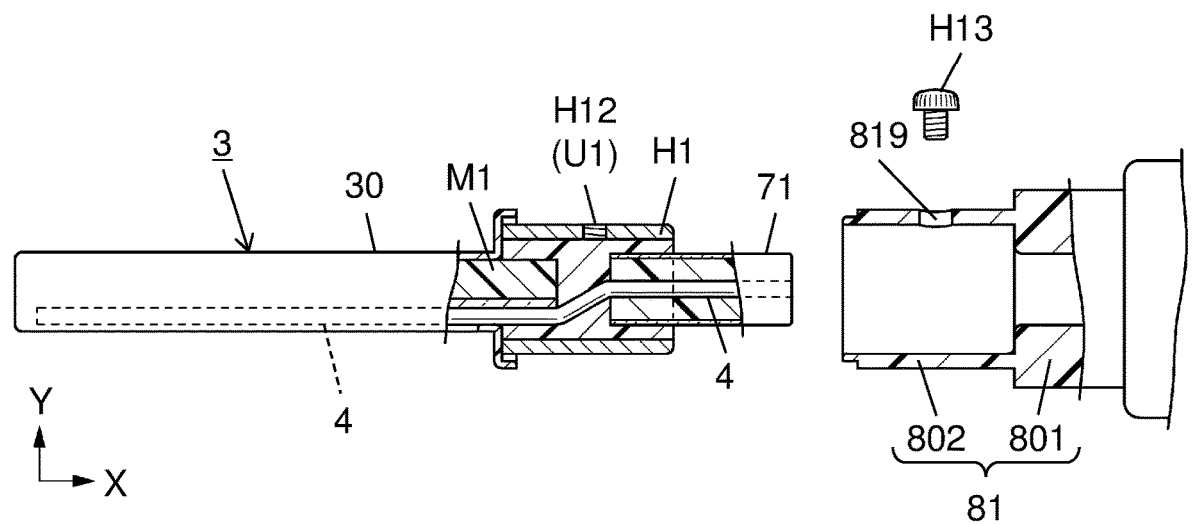
FIG. 14A is a cross-sectional view illustrating a major part of the hair cutting device of the first alternative example according to the third modified example of the exemplary embodiment, showing a state in which the hair cutting member is detached from the device body.
Figure 14B:
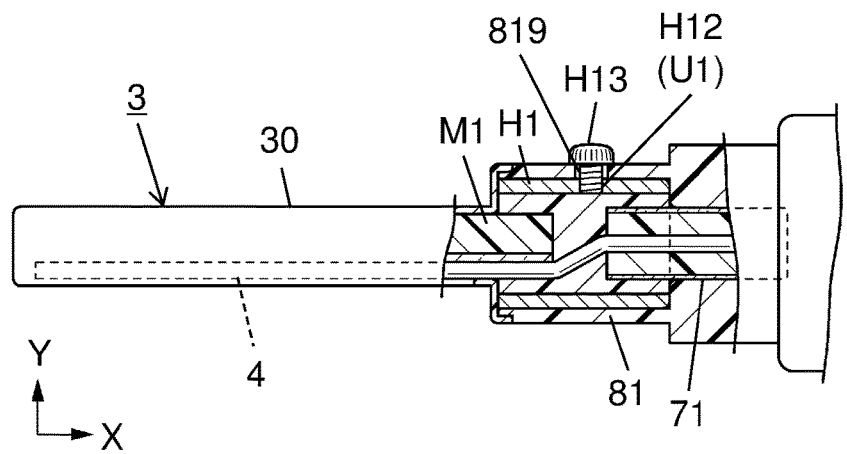
FIG. 14B is a cross-sectional view illustrating a major part of the hair cutting device of the first alternative example according to the third modified example of the exemplary embodiment, showing a state in which the hair cutting member is mounted to the device body.

FIGS. 14A and 14B are cross-sectional views showing a major part of hair cutting device 1 of a first alternative example of the third modified example. FIG. 14A shows a state in which hair cutting member 3 is detached from device body 2. FIG. 14B shows a state in which hair cutting member 3 is attached to device body 2.

As illustrated in FIGS. 14A and 14B, holder H1 may include a restraining structure U1, for example, in place of securing cap 34 and screw part 810 of receptacle 81 in the basic embodiment. In the example shown in FIGS. 14A and 14B, screw hole H12 provided in an outer circumferential portion of holder H1 to penetrate holder H1 toward the inside corresponds to restricting structure U1. Second portion 802 of receptacle 81 is provided with through-hole 819.

Ferrule 71 of hair cutting member 3 is inserted into receptacle 81 and screw H13 is screw-fitted to screw hole H12 through through-hole 819, so that hair cutting member 3 is secured to device body 2 more stably. In the third modified example, restricting structure U1, through-hole 819, and screw H13, which are shown in FIGS. 14A and 14B, are added to hair cutting device 1 shown in FIG. 13A. This makes it possible to prevent unintentional detachment of ferrule 71.

When hair cutting device 1 includes restricting structure U1 and through-hole 819 shown in FIGS. 14A and 14B, it is possible to omit protruding part H11 (positioning structure Q1) of holder H1 and groove 814 (groove 814A). In this case, restricting structure U1 (screw hole H12) shown in FIGS. 14A and 14B also serves as positioning structure Q1.

Figure 13B:
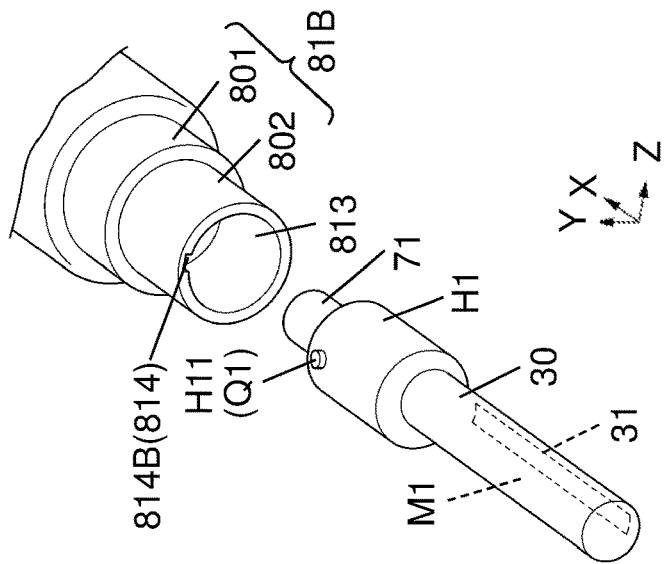
FIG. 13B is a perspective view illustrating a major part of a hair cutting device of a first alternative example according to the third modified example of the exemplary embodiment.

FIG. 13B is a perspective view illustrating a major part of hair cutting device 1 of the first alternative example of the third modified example. As illustrated in FIG. 13B, receptacle 81B includes groove 814B that does not penetrate second portion 802. Groove 814B is a recess disposed in the inner circumferential surface of second portion 802. The amount of protrusion of protruding part H11 from the outer circumferential surface of holder H1 is determined according to the depth of groove 814B, and it is smaller than the amount of protrusion of protruding part H11 in the basic embodiment.

With the configuration of the alternative example of the third modified example, because protruding part H11 (positioning structure Q1) is fitted in groove 814B, it is easy to carry out the circumferential positioning of hair cutting member 3 relative to receptacle 81B. As a result, ease of assembly of hair cutting device 1 is improved.

In FIG. 13B as well, securing cap 34 and screw part 810 screw-fitted to screw thread 341 (restraining structure U1) of securing cap 34 are not shown. Here, restraining structure U1, through-hole 819, and screw H13, which are shown in FIGS. 14A and 14B, are added to hair cutting device 1 shown in FIG. 13B, in place of securing cap 34 and screw part 810 of receptacle 81 in the basic embodiment. This makes it possible to prevent unintentional detachment of ferrule 71.

Figure 13C:
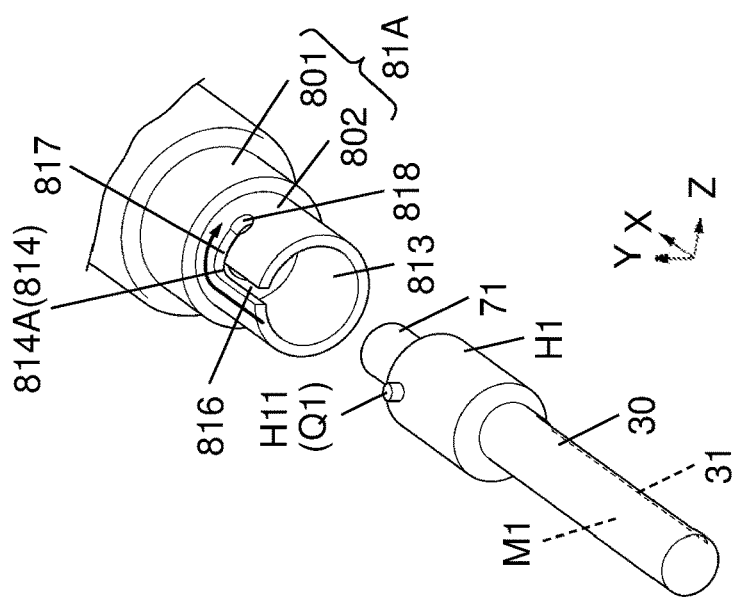
FIG. 13C is a perspective view illustrating a major part of a hair cutting device of a second alternative example according to the third modified example of the exemplary embodiment.

FIG. 13C is a perspective view illustrating a major part of hair cutting device 1 of a second alternative example of the third modified example. As illustrated in FIG. 13C, receptacle 81C is in a polygonal tubular shape having a central axis extending along the X-axis. Specifically, the cross section of receptacle 81C that is parallel to the Y-Z plane has a hexagonal shape. The cross section is plane-symmetrical with respect to the X-Y plane passing through its central axis and asymmetrical with respect to the X-Z plane passing through its central axis.

Second portion 802 of receptacle 81C has larger diameter hole 813 having the same hexagonal shape as its outer contour. Unlike the basic embodiment, second portion 802 does not have groove 814. Smaller diameter hole 812 is a circular shaped penetrating hole, as with the basic embodiment.

The outer contour of holder H1 has substantially the same shape and size of larger diameter hexagonal hole 813 of receptacle 81C, which is a hexagonal shape that can be inserted into larger diameter hole 813 with almost no clearance gap. Unlike the basic embodiment, holder H1 does not have protruding part H11.

With the configuration of the second alternative example of the third modified example, because holder H1 is fitted inside larger diameter hole 813, it is easy to carry out the circumferential positioning of hair cutting member 3 relative to receptacle 81C. As a result, ease of assembly of hair cutting device 1 is improved. In this configuration, holder H1 itself corresponds to positioning structure Q1. For this reason, it is unnecessary to form protruding part H11.

In FIG. 13C as well, securing cap 34 and screw part 810 screw-fitted to screw thread 341 (restraining structure U1) of securing cap 34 are not shown. Here, restraining structure U1, through-hole 819, and screw H13, which are shown in FIGS. 14A and 14B, are added to hair cutting device 1 shown in FIG. 13C, in place of providing securing cap 34 and screw part 810 of receptacle 81 in the basic embodiment. This makes it possible to prevent unintentional detachment of ferrule 71.

Figure 15A:
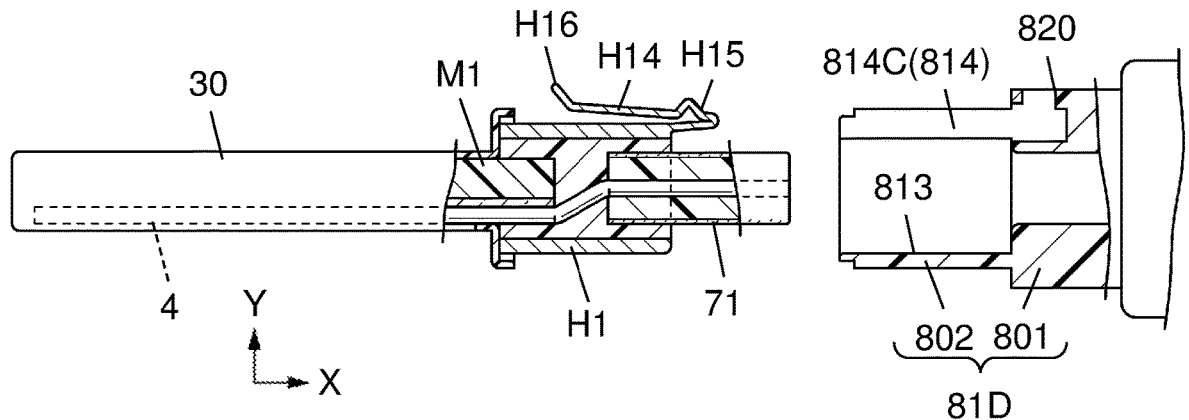
FIG. 15A is a cross-sectional view illustrating a major part of the hair cutting device of the second alternative example according to the third modified example of the exemplary embodiment, showing a state in which the hair cutting member is detached from the device body.
Figure 15B:
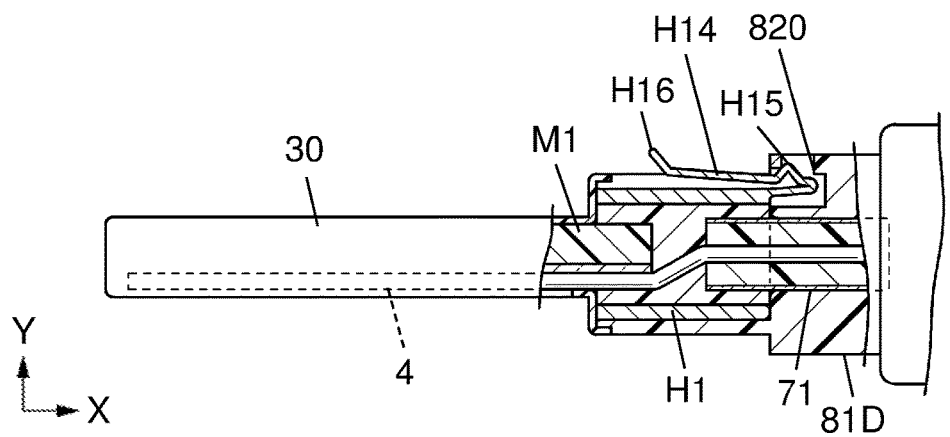
FIG. 15B is a cross-sectional view illustrating a major part of the hair cutting device of the second alternative example according to the third modified example of the exemplary embodiment, showing a state in which the hair cutting member is mounted to the device body.
Figure 15C:
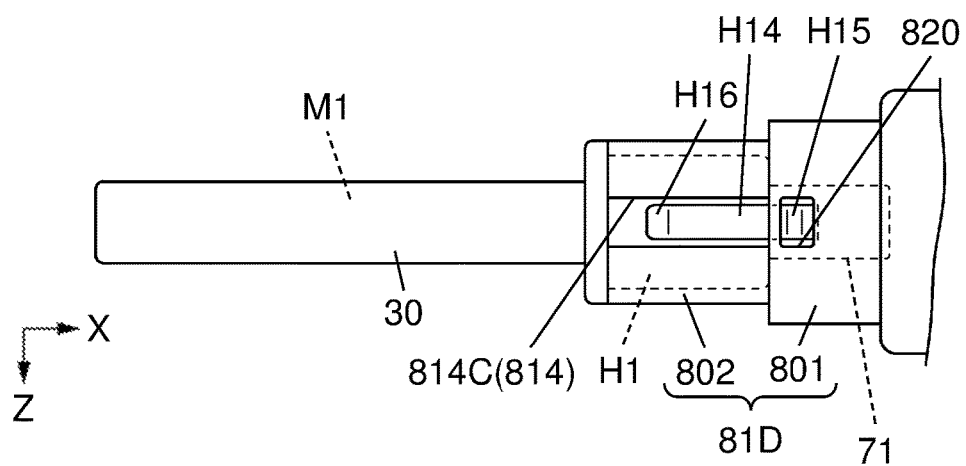
FIG. 15C is a rear view illustrating a major part of the hair cutting device of the second alternative example according to the third modified example of the exemplary embodiment.

FIGS. 15A and 15B are cross-sectional views showing a major part of hair cutting device 1 of the second alternative example of the third modified example. FIG. 15A shows a state in which hair cutting member 3 is detached from device body 2. FIG. 15B shows a state in which hair cutting member 3 is attached to device body 2. FIG. 15C is a rear view illustrating a major part of hair cutting device 1 of the second alternative example of the third modified example.

As illustrated in FIG. 15A to 15C, hair cutting member 3 is attached to device body 2 by a snap fit structure.

Specifically, holder H1 includes hook part H14 in place of protruding part H11 in the basic embodiment. Hook part H14 is a strip plate-shaped member. Hook part H14 has such a shape that it protrudes slightly in the positive direction of the X-axis from an end portion of holder H1 that is on the positive side of the X-axis and is thereafter folded over in the negative direction of the X-axis.

Hook part H14 includes protrusion H15 and operation portion H16. Protrusion H15 is formed in the vicinity of the end portion that is on the positive side of the X-axis. Operation portion H16 is disposed at the tip end that is on the negative side of the X-axis and is tilted in the positive direction of the Y-axis. When the user pushes operation portion H16, the entirety of hook part H14 including protrusion H15 is elastically displaced in the negative direction of the Y-axis.

First portion 801 of receptacle 81D includes hole part 820 onto which protrusion H15 of hook part H14 is hooked. Second portion 802 of receptacle 81D includes groove 814C that guides hook part H14.

To attach hair cutting member 3 to device body 2, hook part H14 of holder H1 is inserted into groove 814C and pressed in the positive direction of the X-axis, and protrusion H15 is hooked onto hole part 820.

To detach hair cutting member 3 from device body 2, holder H1 is moved in the negative direction of the X-axis while pressing operation portion H16, thus causing protrusion H15 to be detached from hole part 820. As a result, ferrule 71 can be pulled out from receptacle 81D.

With the configuration of the second alternative example of the third modified example, because holder H1 is fitted inside larger diameter hole 813, it is easy to carry out the circumferential positioning of hair cutting member 3 relative to receptacle 81C. As a result, ease of assembly of hair cutting device 1 is improved.

The attaching by means of the snap fit structure can prevent detachment of hair cutting member 3 including ferrule 71 to some extent. Adding restraining structure U1, through-hole 819, and screw H13 shown in FIGS. 14A and 14B to hair cutting device 1 shown in FIG. 13C makes it possible to further prevent detachment of hair cutting member 3.

4.4 Fourth Modified Example

Figure 16:
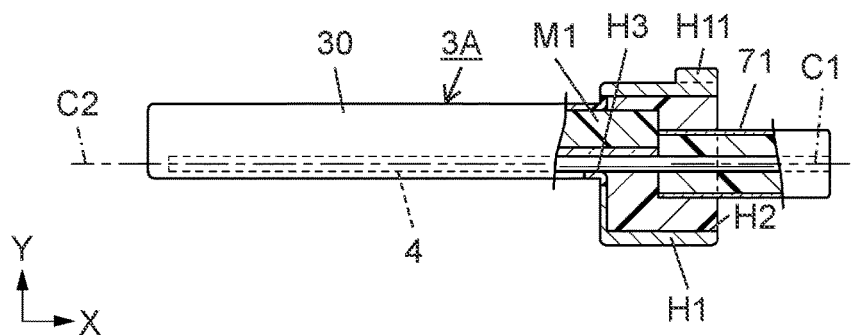
FIG. 16 is a cross-sectional view illustrating a major part of a hair cutting device according to a fourth modified example of the exemplary embodiment.

Hair cutting member 3A according to a fourth modified example of the present exemplary embodiment is described with reference to FIG. 16. FIG. 16 is a cross-sectional view illustrating a major part of hair cutting member 3 in hair cutting device 1 according to the fourth modified example.

As illustrated in FIG. 16, in hair cutting member 3A according to the fourth modified example, optical axis C1 of core 41 positioned by ferrule 71 is coaxial with optical axis C2 of light emitting module M1. In this respect, the fourth modified example is different from the basic embodiment.

Holder H1 of hair cutting member 3A includes circular shaped opening H2 and opening H3 communicating with each other inside holder H1.

Opening H2 is disposed on the positive side of the X-axis of holder H1, that is, on a side thereof on which ferrule 71 is disposed. Opening H3 is disposed on the negative side of the X-axis of holder H1, that is, on a side thereof on which light emitting module M1 is disposed. Opening H2 has the same inner diameter as that of the openings of holder H1 of the basic embodiment. Opening H3 has a smaller inner diameter than opening H2. The inner diameter of opening H3 is substantially equal to the width of light emitting module M1.

The central axis of opening H2 is substantially in agreement with the central axis of entire holder H1. The central axis of opening H3 is shifted from the central axis of opening H2 toward the positive side of the Y-axis. This allows optical axis C1 and optical axis C2 to easily match each other when manufacturing hair cutting member 3A.

Optical axis C1 of core 41 that is positioned by ferrule 71 is coaxial with optical axis C2 of light emitting module M1. This reduces unnecessary light leakage from core 41 in comparison with the basic embodiment, which includes a bent portion (i.e., second region 402).

4.5 Fifth Modified Example

Figure 17:
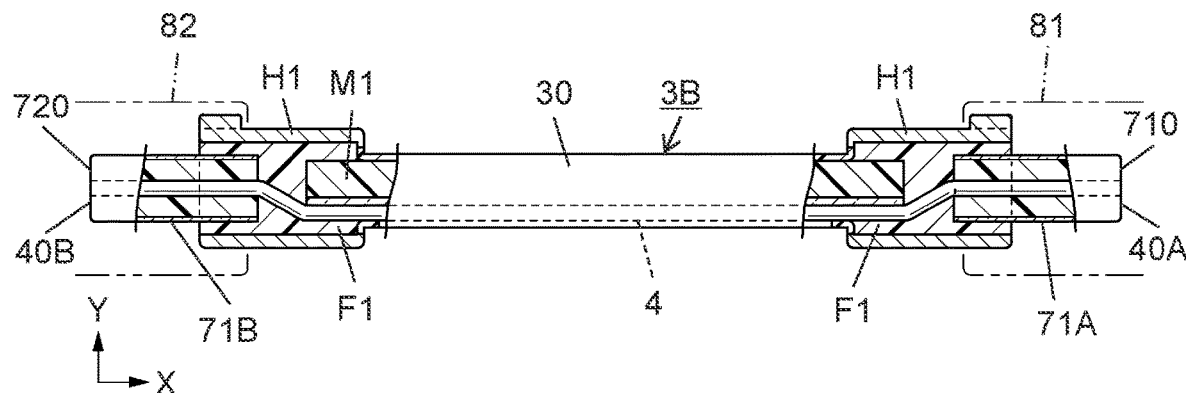
FIG. 17 is a cross-sectional view illustrating a major part of a hair cutting device according to a fifth modified example of the exemplary embodiment.

Hair cutting member 3B according to a fifth modified example of the present exemplary embodiment is described with reference to FIG. 17. FIG. 17 is a cross-sectional view illustrating a major part of hair cutting member 3 in hair cutting device 1 according to the fifth modified example.

As illustrated in FIG. 17, hair cutting member 3B of the fifth modified example further includes second ferrule 71B (second connecting member) in addition to first ferrule 71A (first connecting member), which is ferrule 71 of the basic embodiment.

In the present exemplary embodiment, first ferrule 71A has the same shape and dimensions as second ferrule 71B. As for bonding member G1, the same type of adhesive agent is used for both first ferrule 71A and second ferrule 71B.

Second ferrule 71B is mechanically connectable to second receptacle 81F (second connection target) that is different from first receptacle 81E (first connection target). First receptacle 81E is receptacle 81 of the basic embodiment.

A portion of the light introduced into to core 41 from an end thereof facing first receptacle 81E is led out to another end thereof facing second receptacle 81F. In the present exemplary embodiment, first receptacle 81E and second receptacle 81F have the same shape and dimensions.

Hair cutting member 3B includes two holders H1. Each of the two holders H1 is the same as holder H1 of the basic embodiment. First ferrule 71A is integrally joined to an end portion of the light emitting module that is on the positive side of the X-axis by one set of holder H1 and securing member F1. Second ferrule 71B is integrally joined to an end portion of the light emitting module that is on the negative side of the X-axis by another set of holder H1 and securing member F1.

In hair cutting member 3B, optical waveguide 4 is longer than that of the basic embodiment. Terminal end surface 40B of optical waveguide 4 is flush with end face 720 of second ferrule 71B.

Hair cutting member 3B according to the fifth modified example is joined not only to first receptacle 81E, into which light is introduced, but also to second receptacle 81F, from which light is led out. Second receptacle 81F may be disposed in device body 2, or may also be disposed in an adapter that is provided separately from device body 2 and provided with additional features.

In this configuration, hair cutting member 3B may be attached in an opposite orientation. In other words, first ferrule 71A may be connected to second receptacle 81F and second receptacle 81F may be connected to first ferrule 71A.

In this case, the end face of core 41 on second ferrule 71B side serves as light receiving surface 40A, and the end face of core 41 on first ferrule 71A side serves as terminal end surface 40B. With this configuration, work of attaching hair cutting member 3B can be carried out without paying attention to its orientation.

Figure 18:
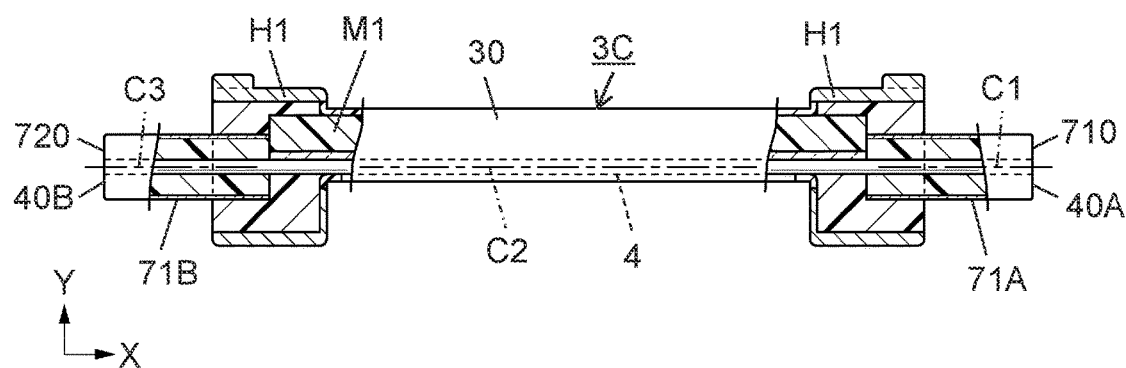
FIG. 18 is a cross-sectional view illustrating a major part of a hair cutting device of an alternative example according to the fifth modified example of the exemplary embodiment.

FIG. 18 is a cross-sectional view illustrating a major part of hair cutting member 3C in hair cutting device 1 of an alternative example of the fifth modified example. As illustrated in FIG. 18, hair cutting member 3C includes two holders H1. Each of two holders H1 is the same as holder H1 of hair cutting member 3A according to the fourth modified example (see FIG. 16).

Optical axis C1 of core 41 that is positioned by first ferrule 71A is coaxial with optical axis C2 of light emitting module M1. Optical axis C3 of core 41 that is positioned by second ferrule 71B is coaxial with optical axis C2 of light emitting module M1. This configuration is able to reduce unnecessary light leakage from core 41.

4.6. Other Modified Examples

As described previously, control circuit 6 of the present exemplary embodiment is composed of a microcomputer. Control circuit 6 is, however, not limited to a microcomputer. Nevertheless, the use of a programmable microcomputer allows the content of processing to be changed easily, increasing the freedom in designing.

In order to increase the processing speed, it is possible that control circuit 6 may be composed of a logic circuit. Control circuit 6 may be physically composed of one or a plurality of elements. When control circuit 6 is composed of a plurality of elements, control items may be executed by respective separate elements. In this case, each of the plurality of elements may be considered as corresponding to control circuit 6.

All the constituent elements of device body 2 may not be accommodated inside one housing. It is possible that the constituent elements of device body 2 may be disposed distributed among a plurality of housings. At least a portion of the constituent elements of control circuit 6 may be implemented by, for example, a server or a cloud.

In the above-described exemplary embodiments, device body 2 (case 20) that can accommodate light source 21 and so forth corresponds to a grip. However, it is also possible that a grip part separate from case 20 may be provided and connected to case 20. The parts to be accommodated inside case 20 may be disposed and distributed in case 20 and the grip part.

Operation portion 26 is not limited to a mechanical switch, but may be a touch switch, an optical or capacitive non-contact switch, or a gesture sensor. Operation portion 26 may be a communication unit configured to receive a command from an external terminal, such as a smartphone. Operation portion 26 may be, for example, a voice input unit configured to accept voice commands from the user.

Hair cutting device 1 may be combined with a shaver that cuts hair 91 with the use of a common blade. In this case, hair cutting device 1 is able to cut hair 91 using the common blade and the light emitted from light emitting portion 40 together.

Optical waveguide 4 is not limited to an optical fiber in which core 41 and cladding 42 are made of synthetic quartz. Optical waveguide 4 may be an optical waveguide 4 made of, for example, quartz ($SiO_2$) or plastic.

Examples of the optical fiber made of plastic include optical fibers in which cladding 42 is made of fluorine-based polymer or the like and core 41 is made of fully fluorinated polymer, polymethyl methacrylate, polycarbonate, or the like. Optical waveguide 4 may be slab waveguide, rectangular optical waveguide, photonic crystal fiber, or the like.

Optical waveguide 4 does not include cladding 42 as long as it includes core 41, which is the minimal configuration. The refractive index of bonding member 52 of retaining member 5 may not necessarily be lower than the refractive index of light emitting portion 40 (core 41).

The refractive index of securing member F1 in holder H1 may not necessarily be lower than the refractive index of core 41. Likewise, the refractive index of bonding member G1 in ferrule 71 may not necessarily be lower than the refractive index of core 41.

Light source 21 may generate light having a plurality of wavelengths, not a single wavelength. In this case, light source 21 may generate lights with a plurality of wavelengths simultaneously, or may generate lights with a plurality of wavelengths one at a time in turns.

In this configuration, light emitted from light emitting portion 40 to hair 91 (i.e., first emission light Op1) is targeted at a plurality of chromophores corresponding to a plurality of wavelengths. This makes it possible to destroy bonds of a plurality of types of molecules. As a result, hair 91 can be cut more efficiently.

Hair cutting member 3 may include a plurality of optical waveguides 4. In this case, hair cutting device 3 is able to cut hair 91 with the lights emitted from respective light emitting portions 40 of the plurality of optical waveguides 4.

Each of the plurality of optical waveguides 4 may pass only one of lights of a plurality of wavelengths. In this case, the plurality of optical waveguides 4 may be disposed toward the center in ferrule 71. Each of the plurality of optical waveguides 4 may be disposed in a corresponding one of a plurality of ferrules 71.

In the present exemplary embodiment, the operating modes of light source 21 are switched manually between the first mode and the second mode. It is possible that the switching between the first mode and the second mode may be performed automatically.

Battery 23 may not be a secondary battery but may be a primary battery. Hair cutting device 1 may receive electric power from a commercial power source, not from a battery.

The power density of the light passing through optical waveguide 4 may be adjusted not by the output from light source 21 but by, for example, an optical filter included in optical system 22 or optical waveguide 4.

It is also possible that the power density of the light passing through optical waveguide 4 may be adjusted by the radius of curvature of optical waveguide 4. It is also possible that the power density of the light passing through optical waveguide 4 may be adjusted by exposing core 41 from a portion of optical waveguide 4 to cause a portion of the light to leak from core 41.

It is also possible that a mirror may be disposed on terminal end surface 40B, which is opposite to light receiving surface 40A of optical waveguide 4. In this case, the mirror is disposed so as to reflect the light that reaches the tip end of optical waveguide 4 to the interior of optical waveguide 4.

The effect on skin 92 is merely a secondary function of hair cutting device 1. It is sufficient that hair cutting device 1 has at least the ability to cut hair 91.

The phrases "greater than or equal to" and "higher than or equal to" that are used to show a relation that makes a comparison between two values may be construed as "greater than" and "higher than", respectively, which do not include the cases in which the two values are equal. Whether or not the phrases include the cases in which the two values are equal depends on the threshold values that are to be set, and there is no technical difference between the two phrases. Likewise, the phrases "lower than or equal to" and "less than or equal to" may be construed as "lower than" and "less than", respectively.

In the present exemplary embodiment, core 41 of hair cutting member 3 is disposed off-center with respect to cladding 42. First distance W1 between center P1 of end face 710 of ferrule 71 and optical axis C1 of core 41 is shorter than second distance W2 between center P1 of end face 710 and center P2 of cladding 42. However, these are not essential for the present disclosure.

As for optical waveguide 4, cladding 42 in first region 401 may be removed entirely so that core 41 can be in direct contact with retaining member 5 (bonding member 52).

Holder H1 is not essential for the present disclosure. For example, securing member F1 alone may join light emitting module M1 and ferrule 71 together. Securing member F1 is not essential for the present disclosure. For example, the inner circumferential surface of holder H1 may be in direct contact with and pressed by the entire outer circumferential surfaces of light emitting module M1 and ferrule 71.

Bonding member G1 is not essential for the present disclosure. For example, the inner circumferential surface of ferrule 71 may be in direct contact with and pressed by the entire outer circumferential surface of optical waveguide 4.

The surface of cladding 42 that comes into contact with bonding member 52, securing member F1, and bonding member G1 may be a roughened surface provided with a large number of recesses and protrusions. The roughened surface as a whole may have various patterns such as pear skin finish, wrinkled patterns (crimps), wood grains, rock grain, sand grains, and geometrical patterns.

Likewise, the surfaces of retaining member 5, holder H1, and ferrule 71 (that come into contact with bonding member 52, securing member F1, and bonding member G1) may each be a roughened surface provided with a large number of recesses and protrusions. In this case, bonding strength (adhesion) is improved by the anchoring effect.

Hair cutting device 1A may include an attachment that is detachably mounted to cover 30 of hair cutting member 3. The attachment may be used to adjust the height of light emitting portion 40 from surface 921 of skin 92.

Light emitting module M1 may be secured by securing member F1 so that its outer circumferential surface is contact with the inner circumferential surface of holder H1. Ferrule 71 may be secured by securing member F1 so that its outer circumferential surface is in contact with the inner circumferential surface of holder H1.

4. Conclusion

A hair cutting member (3, 3A-3C) according to a first aspect includes an optical waveguide (4), a connecting member (ferrule 71), and a bonding member (G1).

The optical waveguide (4) includes a core (41) and a cladding (42) that covers at least a portion of the core (41). The optical waveguide (4) guides light to hair (91) growing on a skin (92). The connecting member (ferrule 71) retains an end of the optical waveguide (4). The bonding member (G1) bonds the optical waveguide (4) and the connecting member (ferrule 71) to each other. The core (41) is disposed off-center toward the outer circumference of the cladding (42).

When viewed from an end face (710) of the connecting member (ferrule 71), the first distance (W1) is a distance between the center (P1) of the end face (710) and the optical axis (C1) of the core (41). The second distance (W2) is a distance between the center (P1) of the end face (710) and the center (P2) of cladding (42). The first distance (W1) is shorter than the second distance (W2). According to the first aspect, adjustment of the optical system in the hair cutting member (3, 3A-3C) is made easier.

In a hair cutting member (3, 3A-3C) according to a second aspect, based on the first aspect, the center (P1) of the end face (710) is located inside the core (41) when viewed from the end face (710). According to the second aspect, the reliability in adjustment of the optical system can be improved.

In a hair cutting member (3, 3A-3C) according to a third aspect, based on the first aspect or the second aspect, the optical axis (C1) of the core (41) is in agreement with the center (P1) of the end face (710) when viewed from the end face (710). According to the third aspect, the reliability in adjustment of the optical system can be improved.

In a hair cutting member (3, 3A-3C) according to a fourth aspect, based on any one of the first aspect to the third aspect, the connecting member (ferrule 71) is mechanically connectable to a connection target (receptacle 81, 81A-81D), and the core (41) is configured so that light is introduced from an end that faces the connection target (receptacle 81, 81A-81D). According to the fourth aspect, ease of assembly is improved, and the optical system can be adjusted easily.

In a hair cutting member (3, 3A-3C) according to a fifth aspect, based on the fourth aspect, the connecting member (ferrule 71) is detachable from the connection target (receptacle 81, 81A-81D). According to the fifth aspect, for example, the hair cutting member (3, 3A-3C) can be replaced easily.

In a hair cutting member (3, 3A-3C) according to a sixth aspect, based on any one of the first aspect to the fifth aspect, a portion of the outer circumferential surface (420) of cladding (42) is disposed so as to be in contact with the inner circumferential surface (711) of the connecting member (ferrule 71). According to the sixth aspect, the core (41) is easily disposed closer toward the center within the connecting member (ferrule 71), and the optical system can be adjusted easily.

In a hair cutting member (3, 3A-3C) according to a seventh aspect, based on any one of the first aspect to the sixth aspect, the core (41) is disposed in an outer circumferential portion of the cladding (42), and a portion of the core (41) is exposed from the outer circumferential portion. According to the seventh aspect, it is unnecessary to remove at least a portion of the cladding (42) to expose the core (41), for example, in a portion of the optical waveguide (4) that is opposed to hair (91) on the skin (92).

In a hair cutting member (3, 3A-3C) according to an eighth aspect, based on any one of the first aspect to the seventh aspect, the refractive index of the bonding member (G1) is lower than the refractive index of the core (41). According to the eighth aspect, it is possible to reduce unnecessary light leakage from the core (41) to the bonding member (G1).

A hair cutting device (1, 1A-1D) according to a ninth aspect includes a hair cutting member (3, 3A-3C) according to any one of the first aspect to the eighth aspect, and a device body (2). The device body (2) includes a connection target (receptacle 81, 81A-81D), a light source (21), an optical system (22), and a case (20).

To the connection target (receptacle 81, 81A-81D), the connecting member (ferrule 71) is mechanically connected. The light source (21) generates light that is to be introduced into the core (41). The optical system (22) is disposed between the light source (21) and the connection target (receptacle 81, 81A-81D). The case (20) is capable of accommodating the light source (21) and the optical system (22).

According to the ninth aspect, the optical system in the hair cutting device (1, 1A-1D) can be adjusted easily.

INDUSTRIAL APPLICABILITY

The hair cutting device according to the present disclosure is applicable to cutting of hairs in various fields, such as cosmetology, medical care, and nursing care.

REFERENCE SIGNS LIST 1, 1A, 1B, 1C, 1D hair cutting device
2 device body
3, 3A, 3B, 3C hair cutting member
4, 4A, 4B optical waveguide
5 retaining member
6 control circuit
20 case
21 light source
22 optical system
23 battery
24 fan
25 heat sink
26, H16 operation portion
30 cover
31 opening
32 securing block
34 securing cap
40 light emitting portion
40A light receiving surface
40B terminal end surface
41 core
42 cladding
43 protruding region
51 base
52, G1 bonding member
53 positioner
61 input unit
62 mode selector
63 output adjuster
64 drive unit
71 ferrule (connecting member)
71A first ferrule (first connecting member)
71B second ferrule (second connecting member)
81, 81A, 81B, 81C, 81D, 83 receptacle
81E first receptacle
81F second receptacle
91 hair
92 skin
221, 222, 223, 224 lens
300 insertion opening
301 flange portion
340 hole
341 screw thread
401, 402, 403 region
420 outer circumferential surface
420A curved surface
511 opposing surface
512 side surface
513 back surface
514 reverse surface
710, 720 end face
711 inner circumferential surface
801, 802 portion
810 screw part
811 through-hole
812 smaller diameter hole
813 larger diameter hole
814, 814A, 814B, 814C groove
816 first groove
817 second groove
818 engaging hole
819 through-hole
820 hole part
921 surface
922 raised portion
C1, C2, C3, CX1 optical axis
F1 securing member
H1 holder
M1 light emitting module
Q1 positioning structure
U1 restraining structure

The invention claimed is:

1. A hair cutting member comprising:
an optical waveguide extending in a first direction and including a core and a cladding covering at least a portion of the core, the optical waveguide guiding light to hair growing on a skin;
a connecting member retaining an end of the optical waveguide; and
a bonding member bonding the optical waveguide and the connecting member to each other, wherein:
in a cross section of the optical waveguide by a plane perpendicular to the first direction, a first part of the core is covered by the cladding and a second part of the core is exposed from the cladding,
the core is disposed off-center toward an outer circumference of the cladding, and
when viewed from an end face of the connecting member, a first distance between a center of the end face and an optical axis of the core is shorter than a second distance between the center of the end face and a center of the cladding.

2. The hair cutting member according to claim 1, wherein the center of the end face is located inside the core when viewed from the end face.

3. The hair cutting member according to claim 1, wherein the optical axis of the core is in agreement with the center of the end face when viewed from the end face.

4. The hair cutting member according to claim 1, wherein the connecting member is mechanically connectable to a connection target, and the core is configured so that light is introduced from an end of the core that faces the connection target.

5. The hair cutting member according to claim 4, wherein the connecting member is detachable from the connection target.

6. The hair cutting member according to claim 1, wherein the cladding is disposed so that a portion of an outer circumferential surface of the cladding is in contact with an inner circumferential surface of the connecting member.

7. The hair cutting member according to claim 1, wherein the core is disposed in an outer circumferential portion of the cladding, and a portion of the core is exposed from the outer circumferential portion.

8. The hair cutting member according to claim 1, wherein a refractive index of the bonding member is lower than a refractive index of the core.

9. A hair cutting device comprising:
the hair cutting member according to claim 1; and
a device body, wherein
the device body comprises:
    a connection target to which the connecting member is mechanically connected;
    a light source configured to generate the light to be introduced into the core;
    an optical system disposed between the light source and the connection target; and
    a case accommodating the light source and the optical system.

* * * * *